(12) United States Patent
Sprunck et al.

(10) Patent No.: US 8,173,864 B2
(45) Date of Patent: May 8, 2012

(54) PLANT EGG CELL TRANSCRIPTIONAL CONTROL SEQUENCES

(75) Inventors: Stefanie Sprunck, Regensburg (DE); Birgit Bellman, Regensburg (DE); Thomas Dresselhaus, Regensburg (DE)

(73) Assignees: Adelaide Research & Innovation Pty Ltd, Adelaide, South Australia (AU); Grains Research & Development Corporation, Kingston, Australian Capital Territory (AU)

( * ) Notice: Subject to any disclaimer, the term of this patent is extended or adjusted under 35 U.S.C. 154(b) by 433 days.

(21) Appl. No.: 12/279,139

(22) PCT Filed: Feb. 13, 2007

(86) PCT No.: PCT/AU2007/000146
§ 371 (c)(1),
(2), (4) Date: Feb. 4, 2009

(87) PCT Pub. No.: WO2007/092992
PCT Pub. Date: Aug. 23, 2007

(65) Prior Publication Data
US 2009/0191635 A1    Jul. 30, 2009

(30) Foreign Application Priority Data

Feb. 13, 2006 (AU) ................................ 2006900681

(51) Int. Cl.
*C12N 15/82* (2006.01)
*C12N 15/29* (2006.01)
*C12N 5/04* (2006.01)
*A01H 5/00* (2006.01)

(52) U.S. Cl. ....... 800/278; 536/24.1; 435/419; 800/287; 800/298

(58) Field of Classification Search ................ None
See application file for complete search history.

(56) References Cited

U.S. PATENT DOCUMENTS 6,337,430 B1 * 1/2002 Ishige et al. ................ 800/278
2004/0016025 A1    1/2004 Budworth et al.

FOREIGN PATENT DOCUMENTS

| CA | 2374375 A1 | 11/2000 |
|---|---|---|
| EP | 0984064 A1 | 3/2000 |
| WO | WO 97/30165 A2 | 8/1997 |
| WO | WO 01/64924 A1 | 9/2001 |
| WO | WO 03/104464 A1 | 12/2003 |

OTHER PUBLICATIONS

Vrinten et al (1999, Plant Molecular Biology 41:455-463).*
Benfey et al (1990, Science 250:959-966).*
Benfey et al (1989, EMBO J, 8(8):2195-2202).*
Lin et al (2000, NCBI Accession No. AC010718).*
Estrada-Luna, A.A., et al., "The activity of specific promoters acting in the ovule of *Arabidopsis* is conserved in the wild Mexican potato *Solanum cardiophyllum* Lindi", *Plant Biology (Rockville)*, vol. 2003, p. 123, abstract (Jul. 2003).
Huanca-Mamani W., et al., "CHR11, a chromatin-remodeling factor essential for nuclear proliferation during female gametogenesis in *Arabidopsis thaliana*", *PNAS*, vol. 102, pp. 17231-17236 (2005).
Sessions, A., et al., Genbank Accession No. CL515996, 1 pg. (Apr. 3, 2004).
Yang, H., at al., "EST sequencing from female gametophytes yields egg-specific promoters and potential signalling molecules", *Plant Biology (Rockville)*, vol. 2005, p. 42, abstract (Jul. 2005).
Yang, W., et al., "An egg apparatus-specific enhancer of *Arabidopsis*, identified by enhancer detection" *Plant Physiology*, vol. 139, pp. 1421-1432 (2005).
Alonso, J.M., et al., Genbank Accession No. BZ382193, 2 pgs. (Nov. 26, 2002).
Bevan, M., et al., Genbank Accession No. AL050351, 43 pgs. (May 27, 1999).
Busch, B.L., Genbank Accession No. AY257863, 12 pgs. (Apr. 10, 2002).
Kaneko, T., et al., Genbank Accession No. AB025637, 14 pgs (Feb. 14, 2004).
Le, Q. et al., "Construction and screening of subtracted cDNA libraries from limited populations of plant cells: a comparative analysis of gene expression between maize egg cells and central cells," *The Plant Journal*, vol. 44, pp. 167-178 (2005).
Lin, X., et al., Genbank Accession No. AC010718, 32 pgs. (Oct. 12, 2000).
Sessions, A., Genbank Accession No. CL49527, 2 pgs. (Apr. 1, 2004).
Town, C., et al., Genbank Accession No. CG947132, 1 pg. (Dec. 15, 2003).
Vrinten, P.L. et al., Genbank Accession No. AF109193, 2 pgs. (Jan. 9, 2000).
Wing, R.A., et al., Genbank Accession No. AC137931, 36 pgs. (Jun. 27, 2003).

* cited by examiner

*Primary Examiner* — Stuart F Baum
(74) *Attorney, Agent, or Firm* — Kilpatrick Townsend & Stockton LLP

(57) ABSTRACT

The present invention relates generally to transcriptional control sequences. Generally, the present invention relates to transcriptional control sequences that specifically or preferentially direct expression of a nucleotide sequence of interest in a plant egg cell. The present invention is predicated, in part, on the identification of transcriptional control sequences derived from EC1 genes which, in preferred embodiments, direct preferential expression in an egg cell of at least one plant taxon.

10 Claims, 8 Drawing Sheets

PLANT EGG CELL TRANSCRIPTIONAL CONTROL SEQUENCES

CROSS-REFERENCES TO RELATED APPLICATIONS

This application is a U.S. National Stage Application of PCT/AU2007/000146, filed Feb. 13, 2007, which claims priority from Australian Patent Application No. 2006900681 filed on Feb. 13, 2006, each of which are incorporated by reference.

FIELD OF THE INVENTION

The present invention relates generally to transcriptional control sequences. Generally, the present invention relates to transcriptional control sequences that specifically or preferentially direct expression of a nucleotide sequence of interest in a plant egg cell.

BACKGROUND OF THE INVENTION

The primary emphasis in genetic modification has been directed to prokaryotes and mammalian cells. For a variety of reasons, plants have proven more intransigent than other eukaryotic cells to genetically manipulate. However, in many instances, it is desirable to effect transcription of an introduced nucleotide sequence of interest either specifically or preferentially in a particular plant part or at a particular developmental stage of the plant. Accordingly, there is substantial interest in identifying transcriptional control sequences, such as promoters or enhancers, which specifically or preferentially direct transcription in particular plant organs, tissues or cell types or at particular developmental stages of the plant.

Expression of heterologous DNA sequences in a plant is dependent upon the presence of an operably linked transcriptional control sequence, such as a promoter or enhancer, which is functional within the plant. The choice of transcriptional control sequence will determine when and where within the organism the heterologous DNA sequence is expressed. For example, where continuous expression is desired throughout the cells of a plant, constitutive promoters are utilized. In contrast, where gene expression in response to a stimulus is desired, an inducible promoter may be used. Where expression in specific tissues or organs is desired, a tissue-specific promoter may be used.

Frequently, it is desirable to effect expression of a DNA sequence in particular cells, tissues or organs of a plant. For example, male and/or female sterility in a plant might be accomplished by genetic manipulation of the plant's genome with a male or female gamete specific promoter operably linked to a toxic protein.

Alternatively, it might be desirable to inhibit expression of a native DNA sequence within particular plant tissues to achieve a desired phenotype. In this case, such inhibition might be accomplished by transformation of the plant with a tissue-specific promoter operably linked to an antisense or RNAi nucleotide sequence, such that expression of these sequences produces an RNA transcript that interferes with translation of the mRNA of the native DNA sequence.

Promoter sequences that can be used to drive egg cell specific expression of a nucleotide sequence of interest in higher plants are not presently available. This may be at least in part attributed to the difficulty in isolating female gametes from seed plants. As a consequence of this difficulty, the transcripts of plant egg cells are poorly represented in current databases of expressed sequence tags (ESTs), which have been mainly generated through sequencing from cDNA libraries produced from complex tissues, e.g. whole floral organs. Though more than 1.5 million Poaceae ESTs were present in the public EST database (by March 2004) the use of complex tissues resulted in under representation of genes expressed at low levels and in only one or a few cell types.

However, the isolation and characterization of egg cell-specific transcriptional control sequences would be desirable for use in the genetic manipulation of plants.

Reference to any prior art in this specification is not, and should not be taken as, an acknowledgment or any form of suggestion that this prior art forms part of the common general knowledge in any country.

SUMMARY OF THE INVENTION

The present invention is predicated, in part, on the identification of transcriptional control sequences derived from EC1 genes which, in preferred embodiments, direct preferential expression in an egg cell of at least one plant taxon.

Accordingly, in a first aspect, the present invention provides an isolated nucleic acid comprising:
   (i) a nucleotide sequence defining a transcriptional control sequence, wherein said transcriptional control sequence is derived from a gene which encodes an EC1 polypeptide; or
   (ii) a nucleotide sequence defining a functionally active fragment or variant of (i).

In accordance with the present invention, a consensus sequence for EC1 polypeptides has been determined. Accordingly, in one particularly preferred embodiment, the isolated nucleic acid of the first aspect of the invention comprises a transcriptional control sequence derived from a gene which encodes a polypeptide comprising the amino acid sequence:

```
[X_N]                                    (SEQ ID NO: 1)
CWXXXXX [LI] X [SH] C [TS] X [DE] [IL] [ILV]
XFF [LIV]

[X_N]                                    (SEQ ID NO: 70)
[LI] XXXCCX [AS] [ILV] XXXXXXCW

[X_N]                                    (SEQ ID NO: 71)
[ILV] G [FL] TXXEXXXLXXXC [X_N]

[X_N]
``` wherein X is any amino acid residue; $[X_N]$ is one or more amino acid residues of any type; [LI] or [IL] is a leucine or isoleucine residue; [SH] is a serine or histidine residue; [TS] is a threonine or serine residue; [DE] is an aspartic acid or glutamic acid residue; [ILV] or [LIV] is a leucine, isoleucine or valine residue; [AS] is an alanine or serine residue; and [FL] is a phenylalanine or leucine residue.

In further preferred embodiments the isolated nucleic acid comprises one or more sequence motifs comprising the nucleotide sequence set forth in SEQ ID NO: 33 and/or SEQ ID NO: 69.

In a preferred form, the transcriptional control sequences of the present invention, or functionally active fragments or variants thereof, are plant egg cell specific or plant egg cell preferential transcriptional control sequences.

In a second aspect, the present invention provides an isolated nucleic acid selected from the list consisting of:
   (i) a nucleic acid comprising the nucleotide sequence set forth in any of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 and SEQ ID NO: 32;

(ii) a nucleic acid comprising a nucleotide sequence which is at least 50% identical to any of the nucleotide sequences mentioned in (i);
(iii) a nucleic acid which hybridizes to any of the nucleic acids mentioned in (i) under stringent conditions;
(iv) a nucleic acid comprising a nucleotide sequence which is the complement or reverse complement of any one of (i) to (iii); and
(v) a fragment of any of (i), (ii), (iii) or (iv).

In a third aspect, the present invention provides a nucleic acid construct comprising the isolated nucleic acid of the first and/or second aspects of the invention.

In a preferred embodiment, the isolated nucleic acid comprises a nucleotide sequence defining a transcriptional control sequence and further comprises a nucleotide sequence of interest operably connected to the transcriptional control sequence. More preferably, the nucleotide sequence of interest is heterologous with respect to said transcriptional control sequence.

In a fourth aspect, the present invention provides a cell comprising:
(i) the nucleic acid construct of the third aspect of the invention; and/or
(ii) a genomically integrated form of the construct mentioned at (i).

In a particularly preferred embodiment, the cell is a plant egg cell. Even more preferably, the level, rate and/or pattern of expression of at least one nucleotide sequence is altered in said plant egg cell relative to a wild type form of said plant egg cell.

In a fifth aspect, the present invention provides a multicellular structure comprising one or more cells of the fourth aspect of the invention. Preferably, the multicellular structure comprises a plant or a part, organ or tissue thereof.

In a sixth aspect, the present invention provides a method for specifically or preferentially expressing a nucleotide sequence of interest in a plant egg cell, the method comprising effecting transcription of the nucleotide sequence of interest in a plant under the transcriptional control of the nucleic acid of any of the first, second, or third aspects of the invention, wherein said nucleic acid comprises a plant egg cell specific or plant egg cell preferential transcriptional control sequence.

In a seventh aspect, the present invention provides a method for promoting female sterility in a plant, the method comprising expressing a nucleotide sequence encoding a cytotoxic or cytostatic protein or a cytotoxic of cytostatic non-translated RNA, specifically or preferentially in an egg cell of the plant; wherein said nucleotide sequence is operably connected to a nucleic acid of any of the first, second or third aspects of the invention and wherein said nucleic acid comprises a plant egg cell specific or plant egg cell preferential transcriptional control sequence.

In an eighth aspect, the present invention provides a method for modulating embryo development and/or embryo size in a plant, the method comprising expressing a nucleotide sequence encoding a transcriptional regulator that acts during embryo development, specifically or preferentially in an egg cell of the plant; wherein said nucleotide sequence encoding a transcriptional regulator is operably connected to a nucleic acid of any of the first, second or third aspects of the invention and wherein said nucleic acid comprises a plant egg cell specific or plant egg cell preferential transcriptional control sequence.

In a ninth aspect, the present invention provides a method for promoting apomixis in a plant, the method comprising expressing an apomixis-promoting nucleotide sequence specifically or preferentially in an egg cell of the plant; wherein said apomixis-promoting nucleotide sequence is operably connected to a nucleic acid of any of the first, second or third aspects of the invention and wherein said nucleic acid comprises a plant egg cell specific or plant egg cell preferential transcriptional control sequence.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to herein by a sequence identifier number (SEQ ID NO:). A summary of the sequence identifiers is provided in Table 1. A sequence listing is provided at the end of the specification.

TABLE 1

Summary of Sequence Identifiers

| Sequence Identifier | Sequence |
|---|---|
| SEQ ID NOS: 1, 70, 71 | EC1 polypeptide consensus amino acid sequences |
| SEQ ID NO: 2 | AtEC1.1 polypeptide amino acid sequence |
| SEQ ID NO: 3 | AtEC1.2a polypeptide amino acid sequence |
| SEQ ID NO: 4 | AtEC1.2b polypeptide amino acid sequence |
| SEQ ID NO: 5 | AtEC1.4 polypeptide amino acid sequence |
| SEQ ID NO: 6 | AtEC1.5 polypeptide amino acid sequence |
| SEQ ID NO: 7 | MtEC1.1 polypeptide amino acid sequence |
| SEQ ID NO: 8 | OsEC1.1 polypeptide amino acid sequence |
| SEQ ID NO: 9 | OsEC1.2 polypeptide amino acid sequence |
| SEQ ID NO: 10 | OsEC1.3 polypeptide amino acid sequence |
| SEQ ID NO: 11 | TaEC1 polypeptide amino acid sequence |
| SEQ ID NO: 12 | HvECA1 polypeptide amino acid sequence |
| SEQ ID NO: 13 | AtEC1.1 open reading frame nucleotide sequence |
| SEQ ID NO: 14 | AtEC1.2a open reading frame nucleotide sequence |
| SEQ ID NO: 15 | AtEC1.2b open reading frame nucleotide sequence |
| SEQ ID NO: 16 | AtEC1.4 open reading frame nucleotide sequence |
| SEQ ID NO: 17 | AtEC1.5 open reading frame nucleotide sequence |
| SEQ ID NO: 18 | MtEC1.1 open reading frame nucleotide sequence |
| SEQ ID NO: 19 | OsEC1.1 open reading frame nucleotide sequence |
| SEQ ID NO: 20 | OsEC1.2 open reading frame nucleotide sequence |
| SEQ ID NO: 21 | OsEC1.3 open reading frame nucleotide sequence |
| SEQ ID NO: 22 | TaEC1 cDNA nucleotide sequence |
| SEQ ID NO: 23 | HvECA1 open reading frame nucleotide sequence |
| SEQ ID NO: 24 | pAtEC1.1 nucleotide sequence |
| SEQ ID NO: 25 | pAtEC1.2a nucleotide sequence |
| SEQ ID NO: 26 | pAtEC1.2b nucleotide sequence |
| SEQ ID NO: 27 | pAtEC1.4 nucleotide sequence |
| SEQ ID NO: 28 | pAtEC1.5 nucleotide sequence |
| SEQ ID NO: 29 | pMtEC1.1 nucleotide sequence |
| SEQ ID NO: 30 | pOsEC1.1 nucleotide sequence |
| SEQ ID NO: 31 | pOsEC1.2 nucleotide sequence |
| SEQ ID NO: 32 | pOsEC1.3 nucleotide sequence |
| SEQ ID NO: 33 | EC1 promoter nucleotide sequence motif #1 |
| SEQ ID NO: 34 | TaGAP1 primer |
| SEQ ID NO: 35 | TaGAP2 primer |
| SEQ ID NO: 36 | TaEC1fw2 primer |
| SEQ ID NO: 37 | TaEC1rev2 primer |
| SEQ ID NO: 38 | Act3fw primer |
| SEQ ID NO: 39 | Act3rev primer |
| SEQ ID NO: 40 | AtEC1.1fw primer |
| SEQ ID NO: 41 | AtEC1.1rev primer |
| SEQ ID NO: 42 | AtEC1.2a/bfw primer |
| SEQ ID NO: 43 | AtEC1.2a/brev primer |
| SEQ ID NO: 44 | AtEC1.4fw primer |
| SEQ ID NO: 45 | AtEC1.4rev primer |
| SEQ ID NO: 46 | AtEC1.5fw primer |
| SEQ ID NO: 47 | AtEC1.5rev primer |
| SEQ ID NO: 48 | pAtEC1.1 primer |
| SEQ ID NO: 49 | AtEC1.1rev1 primer |
| SEQ ID NO: 50 | pAtEC1.2a primer |
| SEQ ID NO: 51 | tAtEC1.2a primer |
| SEQ ID NO: 52 | AtEC1.1-PstI primer |
| SEQ ID NO: 53 | AtEC1.2a-BglII primer |

TABLE 1-continued

Summary of Sequence Identifiers

| Sequence Identifier | Sequence |
|---|---|
| SEQ ID NO: 54 | GUS start rev primer |
| SEQ ID NO: 55 | E1F primer |
| SEQ ID NO: 56 | E1R primer |
| SEQ ID NO: 57 | EC1-PF2 primer |
| SEQ ID NO: 58 | EC1-R primer |
| SEQ ID NO: 59 | GFP-seq primer |
| SEQ ID NO: 60 | LH1 primer |
| SEQ ID NO: 61 | GUS3 primer |
| SEQ ID NO: 62 | GUS4 primer |
| SEQ ID NO: 63 | bar-fw primer |
| SEQ ID NO: 64 | bar-rev primer |
| SEQ ID NO: 65 | 1-1fwXbaI primer |
| SEQ ID NO: 66 | 1-1revXbaI primer |
| SEQ ID NO: 67 | At2a-BgIIIfw primer |
| SEQ ID NO: 68 | At2a-SaIrev primer |
| SEQ ID NO: 69 | EC1 promoter nucleotide sequence motif #2 |

DESCRIPTION OF PREFERRED EMBODIMENTS

It is to be understood that the following description is for the purpose of describing particular embodiments only and is not intended to be limiting with respect to the above description.

As set out above, the present invention is predicated, in part, on the identification of transcriptional control sequences which are derived from EC1 genes that are preferentially expressed in the egg cells of at least some plants.

As used herein, the term "transcriptional control sequence" should be understood as any nucleotide sequence that modulates at least the transcription of an operably connected nucleotide sequence. Furthermore, the transcriptional control sequence of the present invention may comprise any one or more of, for example, a leader, promoter, enhancer or upstream activating sequence.

As referred to herein, the term "transcriptional control sequence" preferably at least includes a promoter.

A "promoter" as referred to herein, encompasses any nucleic acid that confers, activates or enhances expression of an operably connected nucleotide sequence in a cell.

As used herein, the term "operably connected" refers to the connection of a transcriptional control sequence, such as a promoter, and a nucleotide sequence of interest in such as way as to bring the nucleotide sequence of interest under the transcriptional control of the transcriptional control sequence. For example, promoters are generally positioned 5' (upstream) of a nucleotide sequence to be operably connected to the promoter. In the construction of heterologous transcriptional control sequence/nucleotide sequence of interest combinations, it is generally preferred to position the promoter at a distance from the transcription start site that is approximately the same as the distance between that promoter and the gene it controls in its natural setting, i.e. the gene from which the promoter is derived. As is known in the art, some variation in this distance can be accommodated without loss of promoter function.

Accordingly, in a first aspect, the present invention provides an isolated nucleic acid comprising:
(i) a nucleotide sequence defining a transcriptional control sequence, wherein said transcriptional control sequence is derived from a gene which encodes an EC1 polypeptide; or
(ii) a nucleotide sequence defining a functionally active fragment or variant of (i).

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be isolated because that vector, composition of matter, or particular cell is not the original environment of the polynucleotide. An "isolated" nucleic acid molecule should also be understood to include a synthetic nucleic acid molecule, including those produced by chemical synthesis using known methods in the art or by in-vitro amplification (e.g. polymerase chain reaction and the like).

The isolated nucleic acid of the present invention may comprise any polyribonucleotide or polydeoxyribonucleotide, which may be unmodified RNA or DNA or modified RNA or DNA. For example, the isolated nucleic acids of the invention may comprise single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the isolated nucleic acids may comprise triple-stranded regions comprising RNA or DNA or both RNA and DNA. The isolated nucleic acid molecules may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As set out above, the present invention contemplates, among other things, a nucleotide sequence defining a transcriptional control sequence, wherein said transcriptional control sequence is derived from a gene which encodes an EC1 polypeptide. As referred to herein, an "EC1 polypeptide" refers to a polypeptide which is substantially specifically expressed in an egg cell of a plant. Generally, EC1 polypeptides are small (generally less than about 200 amino acid residues) and are putatively secreted. In some embodiments, the EC1 polypeptides contemplated herein further comprise about six conserved cysteine residues and may further comprise a signal peptide for extracellular localization.

The nucleic acids of the present invention comprise nucleotide sequence defining which is "derived from a gene which encodes an EC1 polypeptide". The term "derived from", as it is used herein, refers to a source or origin for the transcriptional control sequence. As such, a transcriptional control sequence "derived from a gene which encodes an EC1 polypeptide" refers to a transcriptional control sequence which, in its native state, exerts at least some transcriptional control over a gene which encodes an EC1 polypeptide in an organism, preferably a plant.

In accordance with the present invention, a consensus EC1 polypeptide sequence has been determined. Accordingly, in one particularly preferred embodiment, the isolated nucleic acid of the first aspect of the invention comprises a transcriptional control sequence derived from a gene which encodes a polypeptide comprising the amino acid sequence:

(SEQ ID NO: 1, 70 and 71)
[X_N]CWXXXXX[LI]X[SH]C[TS]X[DE][IL][ILV]XFF[LIV]
[X_N][LI] XXXCCX[AS][ILV]XXXXXXCW[X_N][ILV]G[FL]
TXXEXXXLXXXC[X_N]

wherein X is any amino acid residue; [X_N] is one or more amino acid residues of any type; [LI] or [IL] is a leucine or isoleucine residue; [SH] is a serine or histidine residue; [TS] is a threonine or serine residue; [DE] is an aspartic acid or glutamic acid residue; [ILV] or [LIV] is a leucine, isoleucine or valine residue; [AS] is an alanine or serine residue; and [FL] is a phenylalanine or leucine residue.

Accordingly, in one embodiment, the present invention provides an isolated nucleic acid comprising:
(i) a nucleotide sequence defining a transcriptional control sequence, wherein said transcriptional control sequence is derived from a gene which encodes a polypeptide comprising the amino acid sequence set forth in (SEQ ID NOS:1, 70 and 71); or (ii) a functionally active fragment or variant of (i).

In further embodiments, the transcriptional control sequence is derived from a gene which encodes a polypeptide comprising the amino acid sequence set forth in any of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11.

In yet further embodiments, the transcriptional control sequence is derived from a gene which comprises an open reading frame comprising the nucleotide sequence set forth in any of SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23.

In specific embodiments, the present invention provides an isolated nucleic comprising a nucleotide sequence defining a transcriptional control sequence, wherein the transcriptional control sequence comprises the nucleotide sequence set forth in any one of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, or a functionally active fragment or variant thereof.

In yet further embodiments the isolated nucleic acid comprises one or more sequence motifs comprising the nucleotide sequence set forth in SEQ ID NO: 33 and/or SEQ ID NO: 69.

As set out above, the present invention also provides a nucleic acid comprising a nucleotide sequence defining a functionally active fragment or variant of the subject transcriptional control sequences.

As referred to herein, a "functionally active fragment or variant" refers to a fragment or variant which retains the functional activity of a transcriptional control sequence.

"Functionally active fragments", as contemplated herein, may be of any length wherein the transcriptional control sequence retains the capability to affect expression of an operably connected nucleotide sequence. The fragment may comprise, for example, at least 50 nucleotides (nt), at least 100 nt or at least 200 nt. For example, in specific embodiments, a fragment at least 50 nt in length comprises fragments which include 50 or more contiguous bases from, for example, the nucleotide sequence of any of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32.

"Functionally active variants" of the transcriptional control sequence of the invention include orthologs, mutants, synthetic variants, analogs and the like which retain the capability to affect expression of an operably connected nucleotide sequence. For example, the term "variant" should be considered to specifically include, for example, orthologous transcriptional control sequences from other organisms; mutants of the transcriptional control sequence; variants of the transcriptional control sequence wherein one or more of the nucleotides within the sequence has been substituted, added or deleted; and analogs that contain one or more modified bases or DNA or RNA backbones modified for stability or for other reasons. "Modified" bases include, for example, tritylated bases and unusual bases such as inosine.

In some embodiments, the functionally active fragment or variant comprises may comprise, for example, at least 50% sequence identity, at least 65% sequence identity, at least 80% sequence identity or at least 95% sequence identity to the nucleotide sequence set forth in any of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32.

When comparing nucleotide sequences to calculate a percentage identity, the compared nucleotide sequences should be compared over a comparison window of at least 50 nucleotide residues, at least 100 nucleotide residues, at least 200 nucleotide residues, at least 500 nucleotide residues or over the full length of any of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms such the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

In some specific embodiments, the transcriptional control sequences provided by the present invention, or functionally active fragments or variants thereof, comprise plant egg cell specific or plant egg cell preferential transcriptional control sequences.

As used herein, a "plant egg cell specific" transcriptional control sequence refers to a transcriptional control sequence which directs the expression of an operably connected nucleotide sequence of interest substantially only in an egg cell of a plant. A "plant egg cell preferential" transcriptional control sequence refers to a transcriptional control sequence which directs the expression of an operably connected nucleotide sequence at a higher level in a plant egg cell than in one or more other tissues of the plant, e.g. leaf tissue or root tissue. Generally, preferential expression in an egg cell includes expression of a nucleotide sequence of interest in a plant egg cell at a level of at least twice, at least 5 times or at least 10 times the level of expression seen in at least one other tissue of a plant, e.g. leaf or root tissue.

As referred to herein, the term "plant egg cell" should be understood to include a cell which is a component of the female gametophyte in a plant. For example, in angiosperm plants, the term "plant egg cell" may include a female gamete, a synergid, a central cell or an antipodal cell of the female gametophyte (embryo sac). In one specific embodiment, the term "plant egg cell" should be understood to refer to a female gamete of a plant.

In a second aspect, the present invention provides an isolated nucleic acid selected from the list consisting of:

(i) a nucleic acid comprising the nucleotide sequence set forth in any of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 and SEQ ID NO: 32;

(ii) a nucleic acid comprising a nucleotide sequence which is at least 50% identical to any of the nucleotide sequences mentioned in (i);

(iii) a nucleic acid which hybridizes to any of the nucleic acids mentioned in (i) under stringent conditions;

(iv) a nucleic acid comprising a nucleotide sequence which is the complement or reverse complement of any one of (i) to (iii); and (v) a fragment of any of (i), (ii), (iii) or (iv).

In one embodiment, the isolated nucleic acid defined at (ii) comprises at least 50% sequence identity, at least 65% sequence identity, at least 80% sequence identity or at least 95% sequence identity to the nucleotide sequence set forth in any of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32.

In another embodiment, the isolated nucleic acid of the second aspect of the invention comprises a nucleotide sequence which defines a transcriptional control sequence or a complement, reverse complement or fragment thereof. In yet another embodiment, the isolated nucleic acid of the second aspect of the invention comprises a nucleotide sequence which defines an egg cell specific or egg cell preferential transcriptional control sequence or a complement, reverse complement or fragment thereof.

As set out at (iii) above, the second aspect of the invention provides isolated nucleic acids which hybridize to any of the nucleic acids mentioned at (i). As used herein, "stringent" hybridisation conditions will be those in which the salt concentration is less than about 1.5 M Na ion, typically about 0.01 to 1.0 M Na ion concentration (or other salts) at pH 7.0 to 8.3 and the temperature is at least 30° C. Stringent conditions may also be achieved with the addition of destabilizing agents such as formamide. Stringent hybridisation conditions may be low stringency conditions, medium stringency conditions or high stringency conditions. Exemplary low stringency conditions include hybridisation with a buffer solution of 30 to 35% formamide, 1 M NaCl, 1% SDS (sodium dodecyl sulphate) at 37° C., and a wash in 1× to 2×SSC (20× SSC=3.0 M NaCl/0.3 M trisodium citrate) at 50 to 55° C. Exemplary moderate stringency conditions include hybridisation in 40 to 45% formamide, 1.0 M NaCl, 1% SDS at 37° C., and a wash in 0.5× to 1×SSC at 55 to 60° C. Exemplary high stringency conditions include hybridisation in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity of hybridisation is also affected by post-hybridization washes, with influencing parameters including the ionic strength and temperature of the final wash solution. For DNA-DNA hybrids, the $T_m$ can be approximated from the equation of Meinkoth and Wahl (*Anal. Biochem.* 138: 267-284, 1984), i.e. $T_m$=81.5° C.+16.6 (log M)+0.41 (% GC)– 0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of different degrees of complementarity. For example, sequences with ≥90% identity can be hybridised by decreasing the $T_m$ by about 10° C. Generally, stringent conditions are selected to be about 5° C. lower than the thermal melting point ($T_m$) for the specific sequence and its complement at a defined ionic strength and pH. However, high stringency conditions can utilize a hybridization and/or wash at, for example, 1, 2, 3, or 4° C. lower than the thermal melting point ($T_m$); medium stringency conditions can utilize a hybridization and/or wash at, for example, 6, 7, 8, 9, or 10° C. lower than the thermal melting point ($T_m$); low stringency conditions can utilize a hybridization and/or wash at, for example, 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (*Laboratory Techniques in Biochemistry and Molecular Biology-Hybridization with Nucleic Acid Probes*, Pt I, Chapter 2, Elsevier, New York, 1993), Ausubel et al., eds. (*Current Protocols in Molecular Biology*, Chapter 2, Greene Publishing and Wiley-Interscience, New York, 1995) and Sambrook et al. (*Molecular Cloning: A Laboratory Manual*, $2^{nd}$ ed., Cold Spring Harbor Laboratory Press, Plainview, N.Y., 1989).

As set out above, the second aspect of the present invention also contemplates nucleic acid fragments.

"Fragments" of a nucleotide sequence may be, for example, at least 5 nucleotides (nt), at least 10 nt, at least 20 nt, at least 50, at least 100, at least 150, at least 200, at least 250, at least 300, at least 350, at least 400, at least 450 or at least 500 nt in length. These fragments have numerous uses that would be evident to one of skill in the art and include, for example, diagnostic probes and primers. Of course, larger fragments, may also be useful, as are fragments corresponding to most, if not all, of the nucleotide sequences set forth in any of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 and SEQ ID NO: 32. For example, a fragment at least 5 nt in length may refer to a fragment which includes 5 or more contiguous bases from, for example, the nucleotide sequence of any of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31 and SEQ ID NO: 32.

The isolated nucleic acids (or fragments or variants thereof) of the present invention may be derived from any source. For example, the nucleic acids may be derived from an organism, such as a plant. Suitable plants include, for example, monocotyledonous angiosperms (monocots), dicotyledonous angiosperms (dicots), gymnosperms and the like.

Exemplary dicots include, for example, *Arabidopsis* spp., *Medicago* spp., *Nicotiana* spp., soybean, canola, oil seed rape, sugar beet, mustard, sunflower, potato, safflower, cassaya, yams, sweet potato, other Brassicaceae such as *Thellungiella halophila*, among others.

In one embodiment, the isolated nucleic acids of the present invention may comprise a transcriptional control sequence derived from a gene which encodes an EC1 polypeptide in an *Arabidopsis* sp. plant. For example the transcriptional control sequences defined herein as pAtEC1.1 (SEQ ID NO: 24), pAtEC1.2a (SEQ ID NO: 25), pAtEC1.2b (SEQ ID NO: 26), pAtEC1.4 (SEQ ID NO: 27) and pAtEC1.5 (SEQ ID NO: 28) are derivable from genes comprising the AtEC1.1 (SEQ ID NO: 13), AtEC1.2a (SEQ ID NO: 14), AtEC1.2b (SEQ ID NO: 15), AtEC1.4 (SEQ ID NO: 16) and AtEC1.5 (SEQ ID NO: 17) open reading frame nucleotide sequences, respectively, from *Arabidopsis thaliana*.

In another embodiment, the isolated nucleic acid of the present invention may comprise a transcriptional control sequence derived from a gene which encodes an EC1 polypeptide in a *Medicago* sp. plant. For example the transcriptional control sequence defined herein as pMtEC1 (SEQ ID NO: 29) is derivable from a gene comprising the MtEC1.1 (SEQ ID NO: 18) open reading frame nucleotide sequence from *Medicago truncatula*.

In further preferred embodiments, the plant is a monocot, more preferably a cereal crop plant.

As used herein, the term "cereal crop plant" includes members of the order Poales, and more preferably the family Poaceae, which produce edible grain for human or animal food. Examples of cereal crop plants that in no way limit the present invention include barley, wheat, rice, maize, millets, sorghum, rye, triticale, oats, teff, rice, spelt and the like. However, the term cereal crop plant should also be understood to include a number of non-Poales species that also produce edible grain, which are known as pseudocereals, and include, for example, amaranth, buckwheat and quinoa.

In one embodiment, the isolated nucleic acid of the present invention may comprise a transcriptional control sequence derived from a gene which encodes an EC1 polypeptide in an *Oryza* sp. plant. For example the transcriptional control sequences defined herein as pOsEC1.1 (SEQ ID NO: 30), pOsEC1.2 (SEQ ID NO: 31) and pOsEC1.3 (SEQ ID NO: 32), are derivable from genes comprising the OsEC1.1 (SEQ ID NO: 19), OsEC1.2 (SEQ ID NO: 20) and OsEC1.2b (SEQ ID NO: 21) open reading frame nucleotide sequences, respectively, from *Oryza sativa*.

In further embodiments, the present invention also contemplates synthetic nucleic acids.

In a third aspect, the present invention provides a nucleic acid construct comprising the isolated nucleic acid of the first and/or second aspects of the invention.

The nucleic acid construct of the present invention may comprise any polyribonucleotide or polydeoxyribonucleotide, which may be unmodified RNA or DNA or modified RNA or DNA. For example, the nucleic acid construct of the invention may comprise single- and/or double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the nucleic acid construct may comprise triple-stranded regions comprising RNA or DNA or both RNA and DNA. The nucleic acid construct may also comprise one or more modified bases or DNA or RNA backbones modified for stability or for other reasons. "Modified" bases include, for example, tritylated bases and unusual bases such as inosine. A variety of modifications can be made to DNA and RNA; thus the term "nucleic acid construct" embraces chemically, enzymatically, or metabolically modified forms.

In one embodiment, the nucleic acid construct comprises DNA. Accordingly, the nucleic acid construct of the present invention may comprise, for example, a linear DNA molecule, a plasmid, a transposon, a cosmid, an artificial chromosome and the like. Furthermore, the nucleic acid construct of the present invention may be a separate nucleic acid molecule or may be a part of a larger nucleic acid molecule.

In another embodiment, the isolated nucleic acid comprises a nucleotide sequence defining a transcriptional control sequence and further comprises a nucleotide sequence of interest operably connected to the transcriptional control sequence.

In some embodiments, the nucleotide sequence of interest is heterologous with respect to the transcriptional control sequence.

As used herein, the term "heterologous with respect to the transcriptional control sequence" refers to the nucleotide sequence of interest being a nucleotide sequence other than that which the transcriptional control sequence is operably connected to in its natural state.

For example, in its natural state, pAtEC1.1 (SEQ ID NO: 24) is operably connected to a gene comprising the AtEC1.1 open reading frame (SEQ ID NO: 13). Accordingly, in this example, any nucleotide sequence other than a nucleotide sequence comprising an open reading frame consisting of the nucleotide sequence set forth in SEQ ID NO: 13 should be considered heterologous with respect to SEQ ID NO: 24. Similarly, any nucleotide sequence other than a nucleotide sequence comprising an open reading frame consisting of the nucleotide sequence set forth in SEQ ID NO: 14 should be considered heterologous with respect to SEQ ID NO: 25; any nucleotide sequence other than a nucleotide sequence comprising an open reading frame consisting of the nucleotide sequence set forth in SEQ ID NO: 15 should be considered heterologous with respect to SEQ ID NO: 26; any nucleotide sequence other than a nucleotide sequence comprising an open reading frame consisting of the nucleotide sequence set forth in SEQ ID NO: 16 should be considered heterologous with respect to SEQ ID NO: 27; any nucleotide sequence other than a nucleotide sequence comprising an open reading frame consisting of the nucleotide sequence set forth in SEQ ID NO: 17 should be considered heterologous with respect to SEQ ID NO: 28; any nucleotide sequence other than a nucleotide sequence comprising an open reading frame consisting of the nucleotide sequence set forth in SEQ ID NO: 18 should be considered heterologous with respect to SEQ ID NO: 29; any nucleotide sequence other than a nucleotide sequence comprising an open reading frame consisting of the nucleotide sequence set forth in SEQ ID NO: 19 should be considered heterologous with respect to SEQ ID NO: 30; any nucleotide sequence other than a nucleotide sequence comprising an open reading frame consisting of the nucleotide sequence set forth in SEQ ID NO: 20 should be considered heterologous with respect to SEQ ID NO: 31; and any nucleotide sequence other than a nucleotide sequence comprising an open reading frame consisting of the nucleotide sequence set forth in SEQ ID NO: 21 should be considered heterologous with respect to SEQ ID NO: 32.

Accordingly, a sequence that is heterologous with respect to a particular transcriptional control sequence may therefore include, for example, orthologous EC1 sequences, reporter genes, selectable marker genes, heterologous protein-encoding nucleic acid sequences; heterologous non-translated RNA encoding nucleic acid sequences and the like.

In a further embodiment, the nucleic acid construct may further comprise a nucleotide sequence defining a transcription terminator.

The term "transcription terminator" or "terminator" refers to a DNA sequence at the end of a transcriptional unit which signals termination of transcription. Terminators are 3'-non-translated DNA sequences generally containing a polyadenylation signal, which facilitates the addition of polyadenylate sequences to the 3'-end of a primary transcript. As with promoter sequences, the terminator may be any terminator sequence which is operable in the cells, tissues or organs in which it is intended to be used. Examples of suitable terminator sequences which may be useful in plant cells include: the nopaline synthase (nos) terminator, the CaMV 35S terminator, the octopine synthase (ocs) terminator, potato proteinase inhibitor gene (pin) terminators, such as the pinII and pinIII terminators and the like.

In one specific embodiment, the nucleic acid construct of the third aspect of the invention comprises an expression cassette comprising the structure:

$$[N]_w\text{-TCS-}[N]_x\text{-Sol-}[N]_y\text{-TT-}[N]_z)$$

wherein:
$[N]_w$ comprises one or more nucleotide residues, or is absent;
TCS comprises the nucleic acid of the first and/or second aspects of the invention, wherein the nucleic acid defines a transcriptional control sequence;
$[N]_x$ comprises one or more nucleotide residues, or is absent;
Sol comprises a nucleotide sequence of interest which encodes an mRNA or non-translated RNA, wherein the nucleotide sequence, Sol, is operably connected to TCS;
$[N]_y$ comprises one or more nucleotide residues, or is absent;
TT comprises a nucleotide sequence defining a transcription terminator;
$[N]_z$ comprises one or more nucleotide residues, or is absent.

The nucleic acid constructs of the present invention may further comprise nucleotide sequences such as, an origin of replication for one or more hosts; a selectable marker gene which is active in one or more hosts and the like.

As used herein, the term "selectable marker gene" includes any gene that confers a phenotype on a cell, in which it is expressed, to facilitate the identification and/or selection of cells which are transfected or transformed with a genetic construct of the invention.

"Selectable marker genes" include any nucleotide sequences which, when expressed by a cell, confer a phenotype on the cell that facilitates the identification and/or selection of transformed cells. A range of nucleotide sequences encoding suitable selectable markers are known in the art. Exemplary nucleotide sequences that encode selectable markers include: antibiotic resistance genes such as ampicillin-resistance genes, tetracycline-resistance genes, kanamycin-resistance genes, the AURI-C gene which confers resistance to the antibiotic aureobasidin A, neomycin phosphotransferase genes (e.g. nptI and nptII) and hygromycin phosphotransferase genes (e.g. hpt); herbicide resistance genes including glufosinate, phosphinothricin or bialaphos resistance genes such as phosphinothricin acetyl transferase encoding genes (e.g. bar, glyphosate resistance genes including 3-enoyl pyruvyl shikimate 5-phosphate synthase encoding genes (e.g. aroA), bromyxnil resistance genes including bromyxnil nitrilase encoding genes, sulfonamide resistance genes including dihydropterate synthase encoding genes (e.g. sul) and sulfonylurea resistance genes including acetolactate synthase encoding genes; enzyme-encoding reporter genes such as GUS and chloramphenicol acetyltransferase (CAT) encoding genes; fluorescent reporter genes such as the green fluorescent protein-encoding gene; and luminescence-based reporter genes such as the luciferase gene, amongst others.

The genetic constructs of the present invention may include further nucleotide sequences intended for the maintenance and/or replication of the genetic construct in prokaryotes or eukaryotes and/or the integration of the genetic construct or a part thereof into the genome of a eukaryotic or prokaryotic cell.

In one embodiment, the construct of the invention is adapted to be at least partially transferred into a plant cell via *Agrobacterium*-mediated transformation. Accordingly, in a further embodiment, the nucleic acid construct of the present invention comprises left and/or right T-DNA border sequences.

Suitable T-DNA border sequences would be readily ascertained by one of skill in the art. However, the term "T-DNA border sequences" should be understood to encompass any substantially homologous and substantially directly repeated nucleotide sequences that delimit a nucleic acid molecule that is transferred from an *Agrobacterium* sp. cell into a plant cell susceptible to *Agrobacterium*-mediated transformation. By way of example, reference is made to the paper of Peralta and Ream (*Proc. Natl. Acad. Sci. USA*, 82(15): 5112-5116, 1985) and the review of Gelvin (*Microbiology and Molecular Biology Reviews*, 67(1): 16-37, 2003).

The present invention also contemplates any suitable modifications to the genetic construct which facilitate bacterial mediated insertion into a plant cell via bacteria other than *Agrobacterium* sp., for example, as described in Broothaerts et al. (*Nature* 433: 629-633, 2005).

Those skilled in the art will be aware of how to produce the constructs described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an *E. coli* cell or a plant cell or an animal cell. Exemplary methods for cloning nucleic acid molecules are described in Sambrook et al. (*Molecular Cloning: A Laboratory Manual*, Cold Spring Harbor Laboratory Press, New York, 2000).

In a fourth aspect, the present invention provides a cell comprising:
 (i) the nucleic acid construct of the third aspect of the invention; and/or
 (ii) a genomically integrated form of the construct mentioned at (i).

The nucleic acid construct may be maintained in the cell as a nucleic acid molecule, as an autonomously replicating genetic element (e.g. a plasmid, cosmid, artificial chromosome or the like) or it may be integrated into the genomic DNA of the cell.

As used herein, the term "genomic DNA" should be understood in its broadest context to include any and all DNA that makes up the genetic complement of a cell. As such, the genomic DNA of a cell should be understood to include chromosomes, mitochondrial DNA, plastid DNA, chloroplast DNA, endogenous plasmid DNA and the like. As such, the term "genomically integrated" contemplates chromosomal integration, mitochondrial DNA integration, plastid DNA integration, chloroplast DNA integration, endogenous plasmid integration, and the like.

The cells contemplated by the fourth aspect of the invention include any prokaryotic or eukaryotic cell.

In one embodiment, the cell is a plant cell. As used herein, the term "plant" includes any plant which comprises an egg cell, including, for example, dicotyledonous or monocotyledonous angiosperms and gymnosperms.

In another embodiment, the plant cell is a dicotyledonous plant cell, for example, an *Arabidopsis* sp. cell. In yet another embodiment the cell is a monocotyledonous plant cell and/or a cereal crop plant cell.

In one specific embodiment, the cell is a plant egg cell. In a further embodiment, the level, rate and/or pattern of expression of at least one nucleotide sequence is altered in the plant egg cell relative to a wild type form of said plant egg cell.

In yet another embodiment, the cell may also comprise a prokaryotic cell. For example the prokaryotic cell may include an *Agrobacterium* sp. cell which carries the nucleic acid construct and which may, for example, be used to transform a plant. In yet another embodiment, the prokaryotic cell may include an *E. coli* cell, which may, for example, be used in the construction or cloning of a nucleic acid construct.

In a fifth aspect, the present invention provides a multicellular structure comprising one or more cells of the fourth aspect of the invention.

In one embodiment, the multicellular structure comprises a plant or a part, organ or tissue thereof.

As referred to herein, "a plant or a part, organ or tissue thereof" should be understood to specifically include a whole plant; a plant tissue; a plant organ; a plant part; plant reproductive material (including, for example, cuttings, seed, flowers, pollen and the like); and cultured plant tissue such as a callus or suspension culture.

The multicellular structure may comprise one or more plant egg cells. For example, the multicellular structure may comprise a plant, a flower, a carpel or pistil, a plant ovary, an ovule or a female gametophyte (embryo sac). In one embodiment, the level, rate and/or pattern of expression of at least one nucleotide sequence is altered in said one or more plant egg cells of the multicellular structure relative to a wild type form of said egg cell.

As set out above, the present invention is predicated, in part, on effecting transcription of the nucleotide sequence of interest under the transcriptional control of the nucleic acid of the first, second or third aspects of the invention, wherein said nucleic acid comprises a transcriptional control sequence.

Accordingly, in a sixth aspect, the present invention provides a method for specifically or preferentially expressing a nucleotide sequence of interest in a plant egg cell, the method comprising effecting transcription of the nucleotide sequence of interest in a plant under the transcriptional control of the nucleic acid of any of the first, second or third aspects of the invention, wherein said nucleic acid comprises a plant egg cell specific or plant egg cell preferential transcriptional control sequence.

Generally, specific or preferential expression of a nucleotide sequence of interest is effected by introducing said nucleic acid into a plant cell such that the nucleotide sequence of interest is operably connected to a transcriptional control sequence of the present invention.

The present invention contemplates any method to effect operable connection of a nucleotide sequence of interest to the transcriptional control sequence of the invention. For example, a nucleotide sequence of interest may be incorporated into the nucleic acid molecule that comprises the transcriptional control sequence, and be operably connected thereto. In this way, the nucleotide sequence of interest and transcriptional control sequence are both introduced into the plant. Alternatively, the nucleic acid sequence of the present invention may be inserted into the plant genome such that it is placed in operable connection with an endogenous EC1 transcriptional control sequence. As would be recognised by one of skill in the art, the insertion of the transcriptional control sequence into the plant genome may be either by non-site specific insertion or by site-specific insertion (for an example of site-specific insertion see Terada et al., *Nat Biotechnol* 20: 1030-1034, 2002).

The nucleic acid may be introduced into a plant via any suitable method. For example, an explant or cultured plant tissue may be transformed with a nucleic acid molecule, and the transformed explant or cultured plant tissue subsequently regenerated into a mature plant which produces seed including the nucleic acid molecule; a nucleic acid may be directly transformed into a plant, either stably or transiently; a nucleic acid may be introduced into a plant via breeding using a parent plant that carries the nucleic acid molecule; and the like.

In one embodiment, the nucleic acid molecule is introduced into a plant cell via transformation. Plant cells may be transformed using any method known in the art that is appropriate for the particular plant species. Common methods include *Agrobacterium*-mediated transformation, microprojectile bombardment based transformation methods and direct DNA uptake based methods. Roa-Rodriguez et al. (Agrobacterium-mediated transformation of plants, 3$^{rd}$ Ed. CAMBIA Intellectual Property Resource, Canberra, Australia, 2003) review a wide array of suitable *Agrobacterium*-mediated plant transformation methods for a wide range of plant species. Microprojectile bombardment may also be used to transform plant tissue and methods for the transformation of plants, particularly cereal plants, and such methods are reviewed by Casas et al. (*Plant Breeding Rev.* 13: 235-264, 1995). Direct DNA uptake transformation protocols such as protoplast transformation and electroporation are described in detail in Galbraith et al. (eds.), *Methods in Cell Biology* Vol. 50, Academic Press, San Diego, 1995). In addition to the methods mentioned above, a range of other transformation protocols may also be used. These include infiltration, electroporation of cells and tissues, electroporation of embryos, microinjection, pollen-tube pathway, silicon carbide- and liposome mediated transformation. Methods such as these are reviewed by Rakoczy-Trojanowska (*Cell. Mol. Biol. Lett.* 7: 849-858, 2002). A range of other plant transformation methods may also be evident to those of skill in the art and, accordingly, the present invention should not be considered in any way limited to the particular plant transformation methods exemplified above.

The nucleotide sequence of interest, which is placed under the regulatory control of the transcriptional control sequence of the present invention, may include any nucleotide sequence of interest. General categories of nucleotide sequences of interest may include, for example:

(i) cytotoxin genes such as barnase, RNase or diphtheria toxin which may be used to induce female sterility and/or embryoless fruits in a plant;
 (ii) genes encoding transcriptional regulators acting during later stages of embryo development such as BBM or LEC1/LEC2, AP2 transcription factors which may be used to modify embryo development and/or increase embryo size;
 (iii) genes encoding cell cycle regulators such as RB or E2F, transcriptional regulators acting during later stages of embryo development such as BBM, LEC1/LEC2 or chromatin remodelling factors such as DNA methyltransferases, histone modifying enzymes and the like, which may be used to effect apomictic embryo development (e.g. parthenogenesis; autonomous embryogenesis);
 (iv) reporter genes, such as those encoding GUS, GFP and the like;
 (v) genes involved in cellular metabolism such as Zinc finger proteins, kinases, heat shock proteins and the like;
 (vi) genes involved in agronomic traits such as disease or pest resistance or herbicide resistance;
 (vii) genes involved in grain characteristics such as grain biomass, nutritional value, post-harvest characteristics and the like;

(viii) genes encoding heterologous proteins, such as proteins encoding heterologous enzymes or structural proteins or proteins involved in biosynthetic pathways for heterologous products;

(ix) nucleotide sequences encoding non-translated RNA, for example an siRNA, miRNA, antisense RNA and the like.

Generally, the nucleotide sequence of interest is heterologous with respect to the transcriptional control sequence.

In a seventh aspect, the present invention provides a method for promoting female sterility in a plant, the method comprising expressing a nucleotide sequence encoding a cytotoxic or cytostatic protein or a cytotoxic of cytostatic non-translated RNA, specifically or preferentially in an egg cell of the plant; wherein said nucleotide sequence is operably connected to a nucleic acid of any of the first, second or third aspects of the invention and wherein said nucleic acid comprises a plant egg cell specific or plant egg cell preferential transcriptional control sequence.

As referred to herein, the "cytotoxic or cytostatic protein" or "cytotoxic or cytostatic non-translated RNA" refers to any protein or non-translated RNA that inhibits or prevents the growth, division, metabolic function or fertilization of the egg cell. In some embodiments, the nucleotide sequence encodes a cytotoxic protein selected from the list consisting of a barnase, an RNAse or a diphtheria toxin.

In an eighth aspect, the present invention provides a method for modulating embryo development and/or embryo size in a plant, the method comprising expressing a nucleotide sequence encoding a transcriptional regulator that acts during embryo development, specifically or preferentially in an egg cell of the plant; wherein said nucleotide sequence encoding a transcriptional regulator is operably connected to a nucleic acid of any of the first, second or third aspects of the invention and wherein said nucleic acid comprises a plant egg cell specific or plant egg cell preferential transcriptional control sequence.

In one embodiment, the nucleotide sequence encoding a transcriptional regulator comprises a transcriptional regulator which acts during later stages of embryo development, more preferably the transcriptional regulator comprises a BBM, LEC1/LEC2, AP2 or other transcription factor.

In a ninth aspect, the present invention provides a method for promoting apomixis in a plant, the method comprising expressing an apomixis-promoting nucleotide sequence specifically or preferentially in an egg cell of the plant; wherein said apomixis-promoting nucleotide sequence is operably connected to a nucleic acid of the first second or third aspects of the invention and wherein said nucleic acid comprises a plant egg cell specific or plant egg cell preferential transcriptional control sequence.

As used herein, the term "apomixis-promoting nucleotide sequence" includes any nucleotide sequence which promotes apomixis when expressed in a plant, and, more particularly, when expressed in a plant egg cell. The apoxmis-promoting nucleotide sequence may include, for example, a nucleotide sequence which encodes any of:

(i) a cell cycle regulator, such as RB or E2F;
(ii) a transcriptional regulator that acts during later stages of embryo development, such as BBM, LEC1/LEC2;
(iii) a chromatin remodeling factor such as a DNA methyltransferase; or
(iv) a histone modifying enzyme.

The methods of the sixth, seventh, eighth and ninth aspects of the present invention may be performed using any suitable plant. However, in one preferred embodiment, the plant is a dicotyledonous plant and, in another embodiment, an *Arabidopsis* sp. plant. In further embodiments, the plant may be a monocotyledonous plant and/or a cereal crop plant.

Finally, reference is made to standard textbooks of molecular biology that contain methods for carrying out basic techniques encompassed by the present invention, including DNA restriction and ligation for the generation of the various genetic constructs described herein. See, for example, Maniatis et al., *Molecular Cloning: A Laboratory Manual* (Cold Spring Harbor Laboratory Press, New York, 1982) and Sambrook et al. (2000, supra).

The present invention is further described by the following non-limiting examples:

Figure 6:
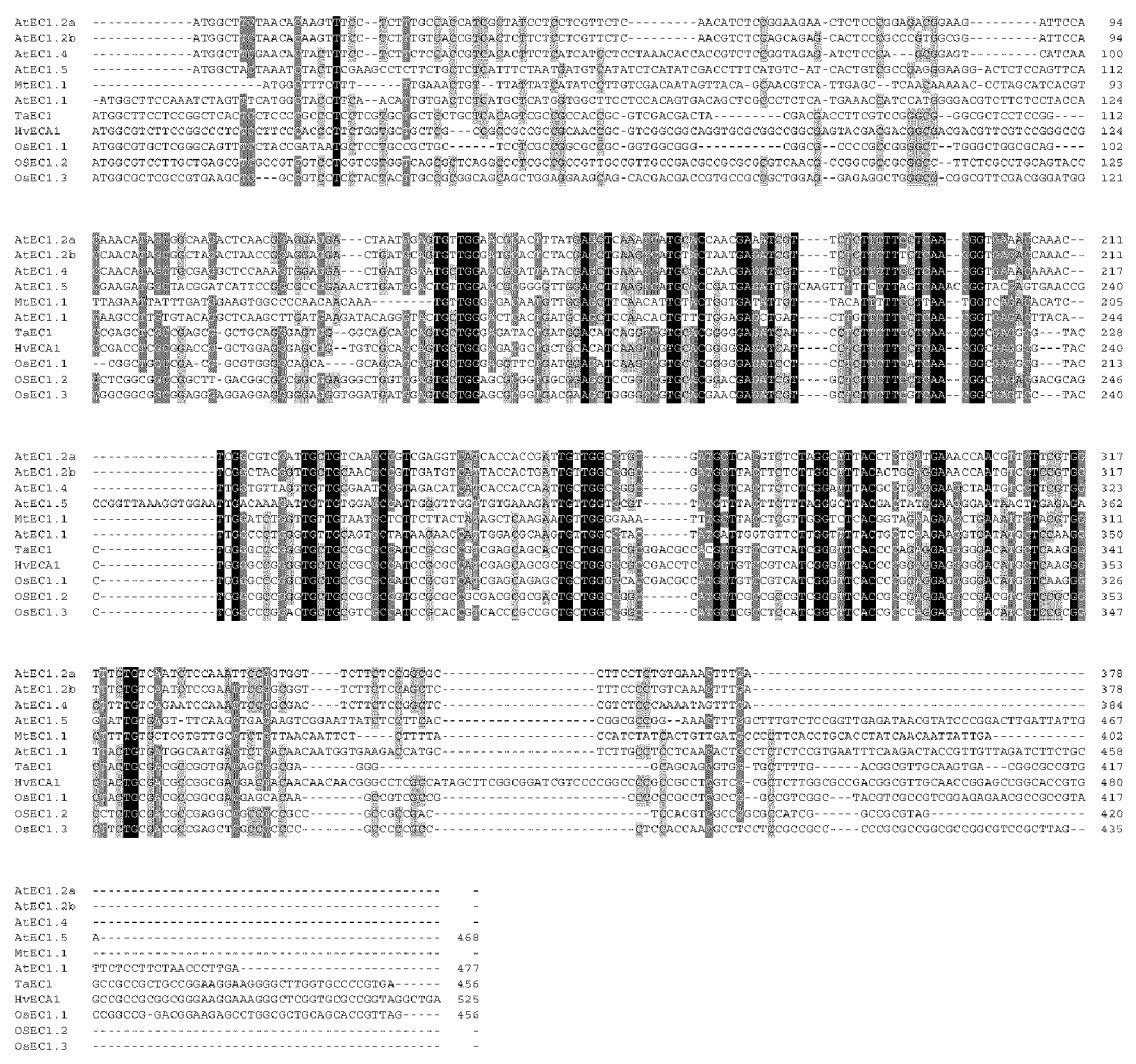

FIG. 6 shows an alignment of EC1 cDNA and predicted genomic sequences encoding open reading frames (ORFs) derived from wheat (TaEC1) (SEQ ID NO:74), barley (HvECA1) (SEQ ID NO:23), rice (OsEC1) (SEQ ID NOS: 19-21), Medicao truncatula (MtEC1) (SEQ ID NO:18) and Arabidopsis (AtEC1) (SEQ ID NOS:14-17 and 13).

Figure 7:
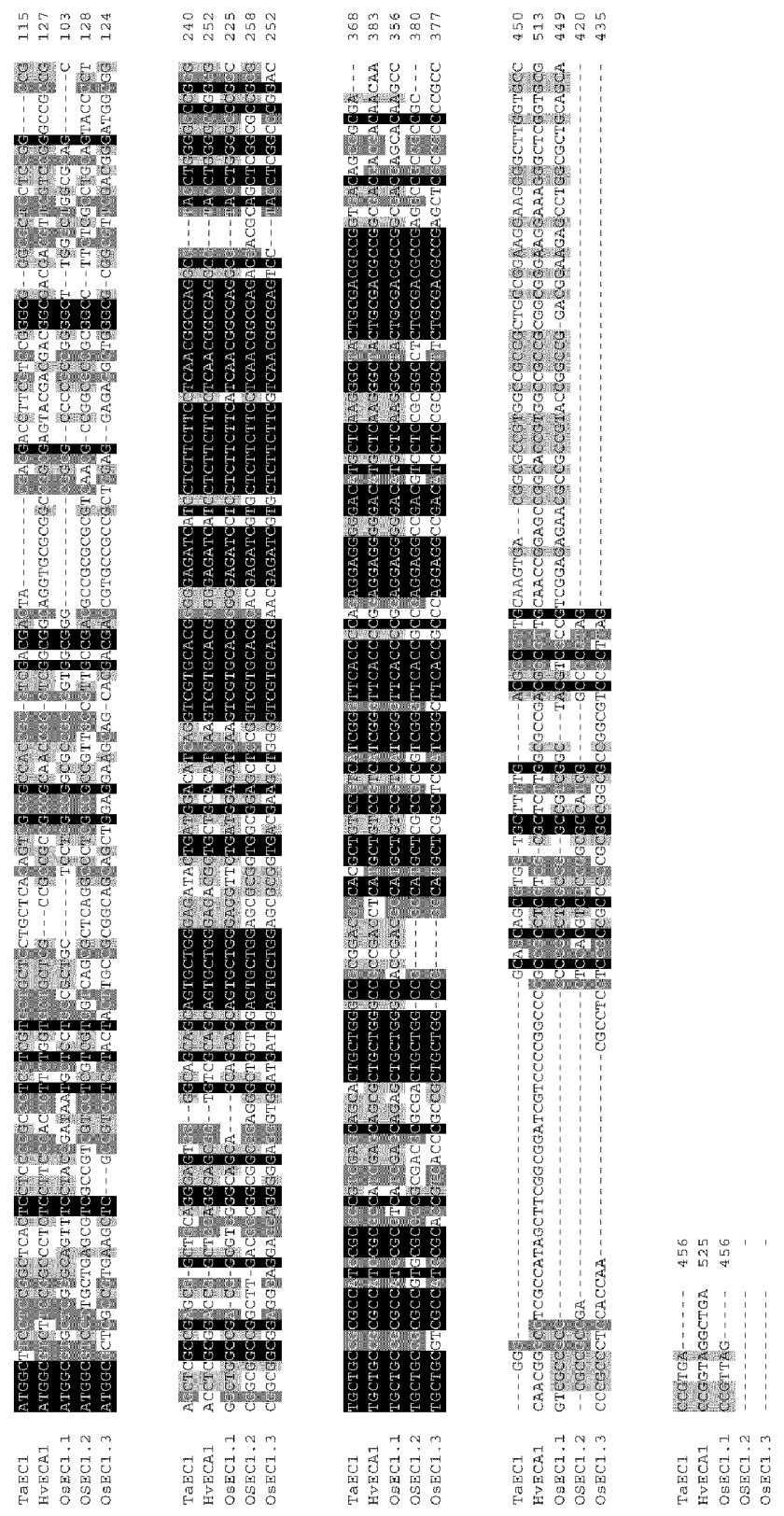

FIG. 7 shows an alignment of EC1 ORFs derived from cereal cDNA and predicted genomic sequences (SEQ ID NOS:74, 23, and 19-21).

Figure 8:
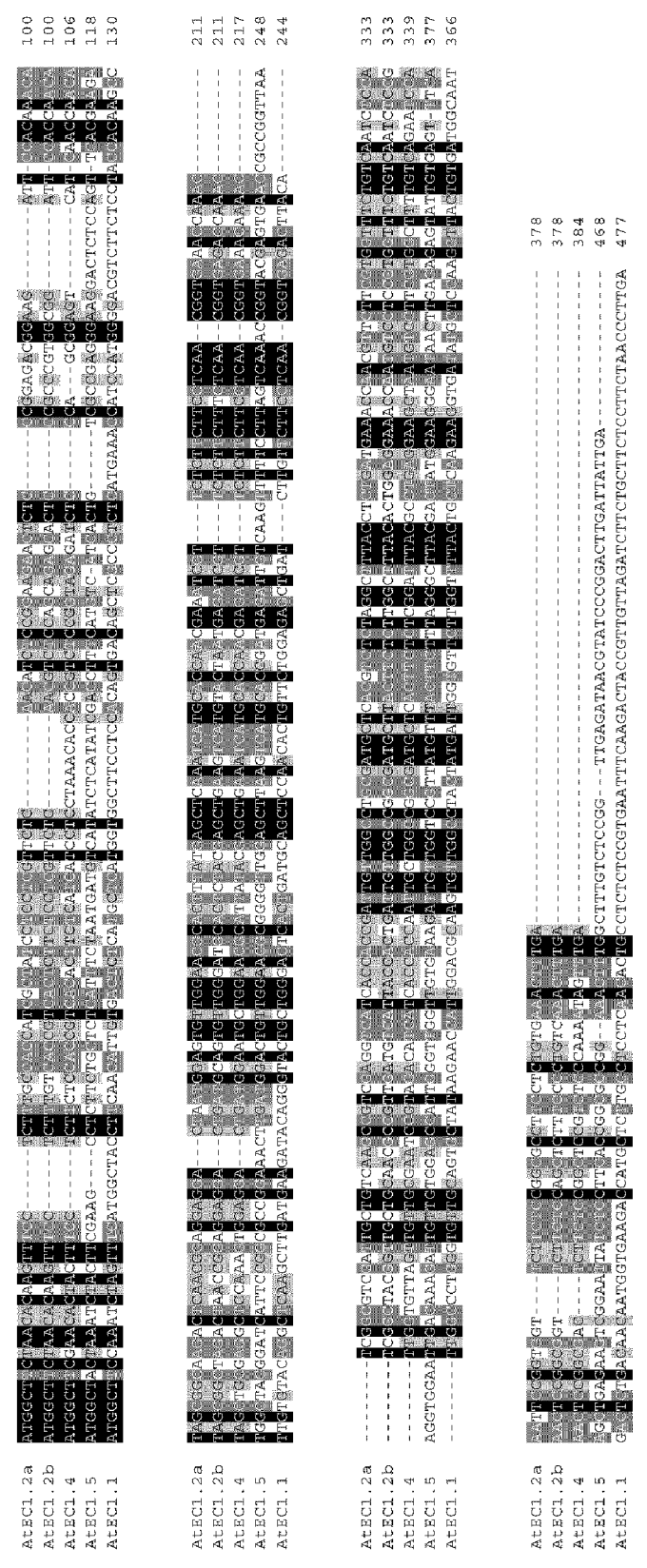

FIG. 8 shows an alignment of EC1 predicted ORFs derived from Arabidopsis thaliana genomic sequences (SEQ ID NOS:14-17 and 13).

Figure 9:
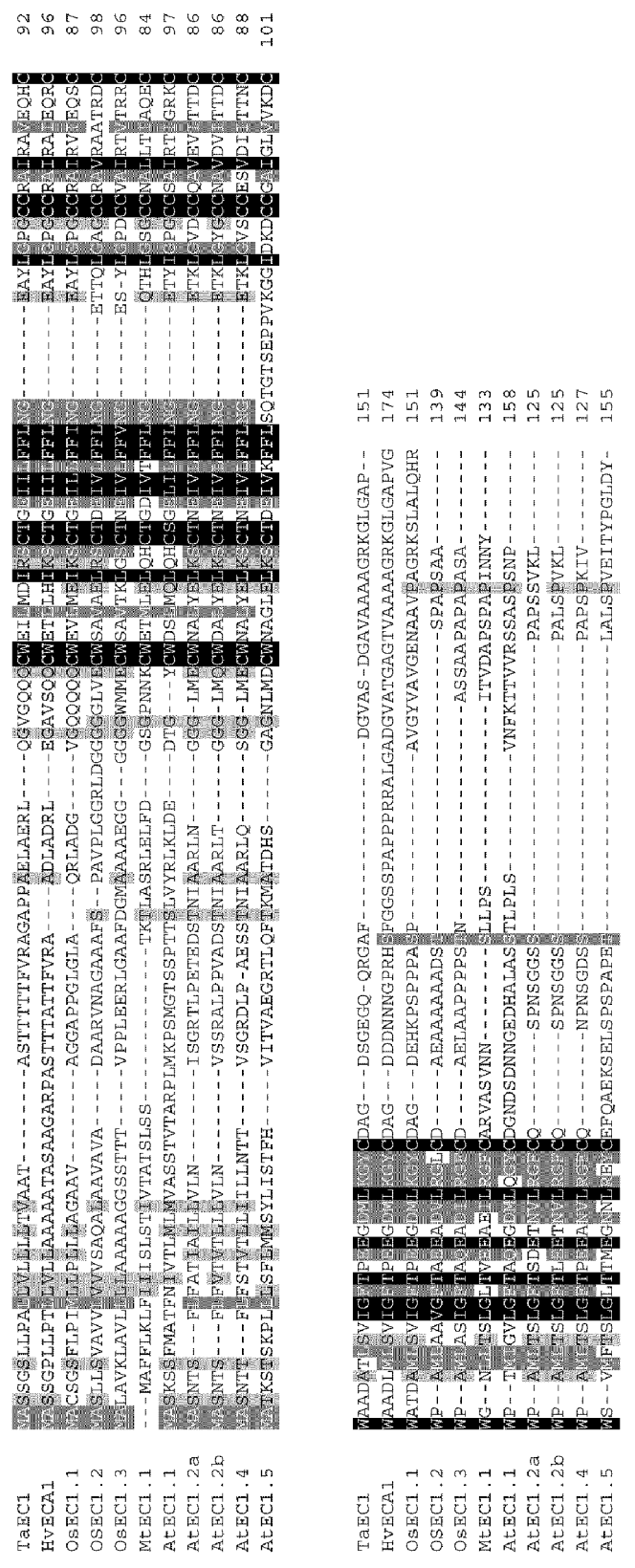

FIG. 9 shows a protein-alignment of EC1 proteins from wheat (TaEC1) (SEQ ID NO:11), barley (HvECA1) (SEQ ID NO:12), rice (OsEC1) (SEQ ID NOS:8-10), Arabidopsis (AtEC1) (SEQ ID NOS:2-6) and Medicago truncatula (MtEC1.1) (SEQ ID NO:7).

Figure 10:
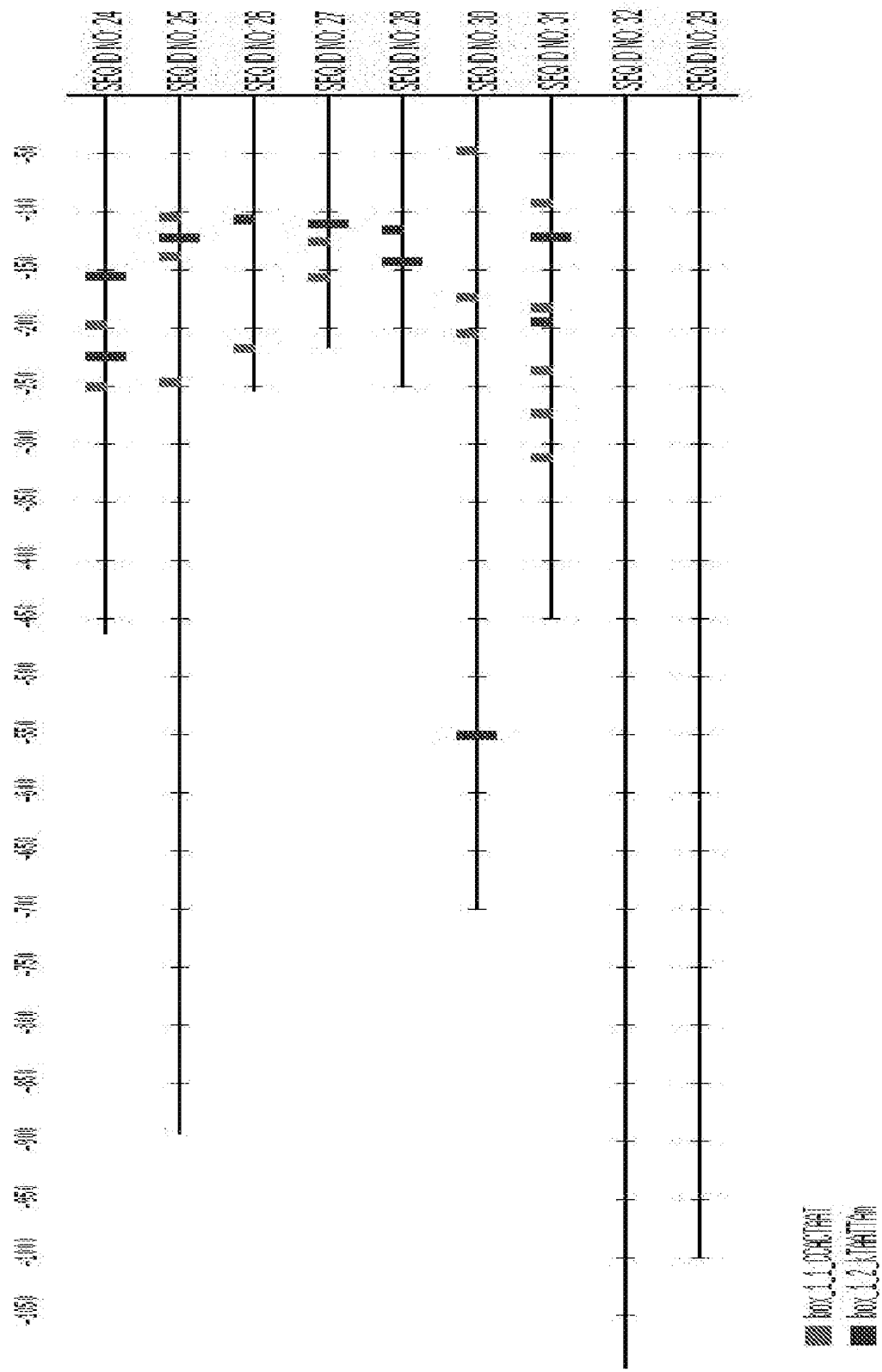

FIG. 10 is a graphical representation showing novel overrepresented motifs in the upstream region of egg cell specific expressed genes identified by MotifSampler. The motif finding algorithm uses Gibbs sampling to find the position probability matrix that represents the motif.

EXAMPLE 1

Identification of Genes Specifically Expressed in Plant Egg Cells

To order to identify genes that are specifically expressed in the egg cell, female gametophytes of wheat were initially microdissected to isolate egg cells. Using the messenger RNA from 12 egg cells, a cDNA library was constructed and single-run partial sequencing of 960 randomly selected cDNA clones was performed. After DNA sequencer trace data passed an automated cleanup pipeline, a total of 735 ESTs were used for bioinformatical analysis. The 735 ESTs formed 404 independent clusters including 310 singletons.

The consensus sequences of the clusters were used for BLASTN and BLASTX searches at the NCBI nonredundant database (nr), dbEST and SwissProt database. Some cDNA sequences resulted in limited sequence information from non-coding regions. Therefore, searches were performed against the TIGR Wheat Gene Index Release 8.0, using the BLASTN algorithm. If a match with >95% sequence identity over the total length of the query sequence was found, the matching sequence was retrieved and used in subsequent BLASTX searches in place of the original EST. BLASTN searches against the NCBI database category of non-mouse and non-human ESTs resulted in 629 egg cell ESTs (333 clusters) matching significantly to annotated ESTs mainly generated from different vegetative tissues of wheat, barley or rice (NCBI dbEST Poaceae). 106 egg cell ESTs (71 clusters) did not match annotated ESTs and were thus considered as "novel" transcripts.

Transcripts were selected which did not match to any EST generated from vegetative plant tissues, and which matched to so-called "hypothetical" proteins (computer-predicted open reading frames from the Arabidopsis and/or rice genome sequences). It was assumed that the corresponding genes of some of these transcripts might be specifically expressed in egg cells of seed plants.

Significant similarities to "hypothetical" proteins of Arabidopsis and/or rice were identified for 98 egg cell clusters. Of these, 11 clusters were not similar to any published EST but only to annotated "hypothetical" genes detected in genomes of Arabidopsis and/or rice and it was concluded that these might be candidate genes that are specifically or preferentially expressed in the female gametes or gametophyte of Arabidopsis and/or rice.

Using this strategy a very large cluster of transcripts from the wheat egg cell (TaEC1) was identified, which did not match to ESTs from any vegetative tissues, but which displayed significant similarity to hypothetical proteins from Arabidopsis, Medicago truncatula and rice. In total, there are five TaEC1-like hypothetical genes in Arabidopsis, which are located on chromosomes 1, 2, 4 and 5. These were designated AtEC1.1 (SEQ ID NO: 13), AtEC1.2a (SEQ ID NO: 14), AtEC1.2b (SEQ ID NO: 15), AtEC1.4 (SEQ ID NO: 16) and AtEC1.5 (SEQ ID NO: 17). One hypothetical TaEC1-like gene in Medicago truncatula was designated MtEC1.1 (SEQ ID NO: 18) and three hypothetical TaEC1-like genes in rice are located on chromosomes 3, 11, and 12 and were designated OsEC1.1 (SEQ ID NO: 19), OsEC1.2 (SEQ ID NO: 20) and OsEC1.3 (SEQ ID NO: 21).

Figure 1:
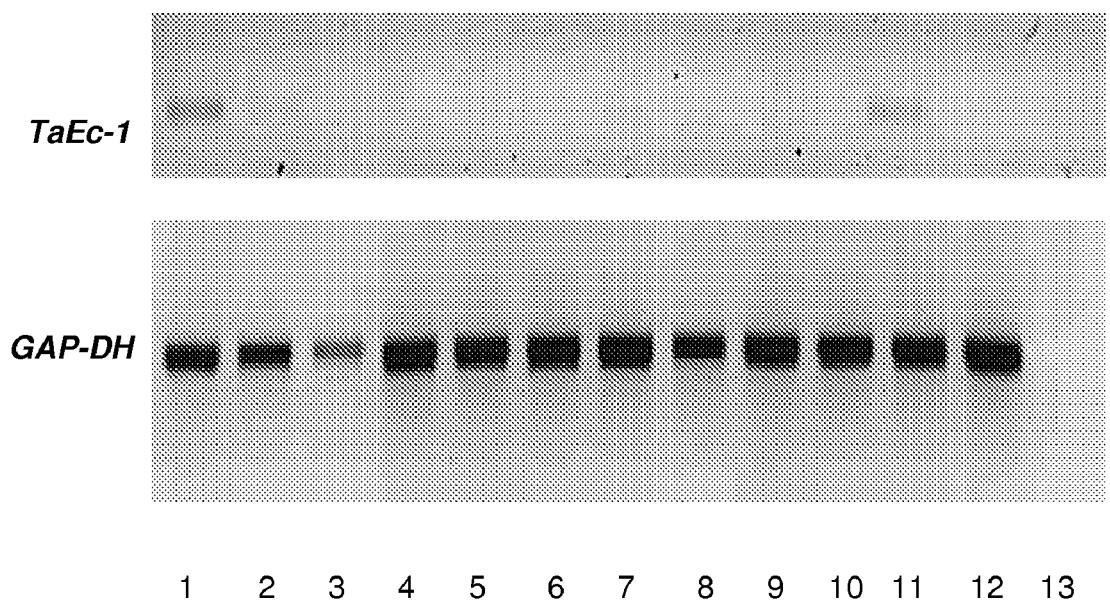
FIG. 1 shows an expression profile of C06_3 transcripts (TaEC1) originally derived from the wheat egg cell cDNA library. Expression of TaEC1 was examined by RT-PCR using DNAse treated total RNA from different tissues of wheat and gene specific primers for C06_3. As controls, cDNA from egg cells, central cells and 2-celled pro-embryos have been used. Quality and quantity of generated cDNA was verified using primers for the ubiquitously expressed GAP-DH. Lane 1: egg cell, 2: pro-embryo, 3: central cell, 4: coleoptile, 5: primary leaf, 6: mature leaf, 7: stem, 8: root without tip, 9: root tip, 10: anther, 11: pistil, 12: kernel 12 dap (days after pollination), 13: negative control.
Figure 2:
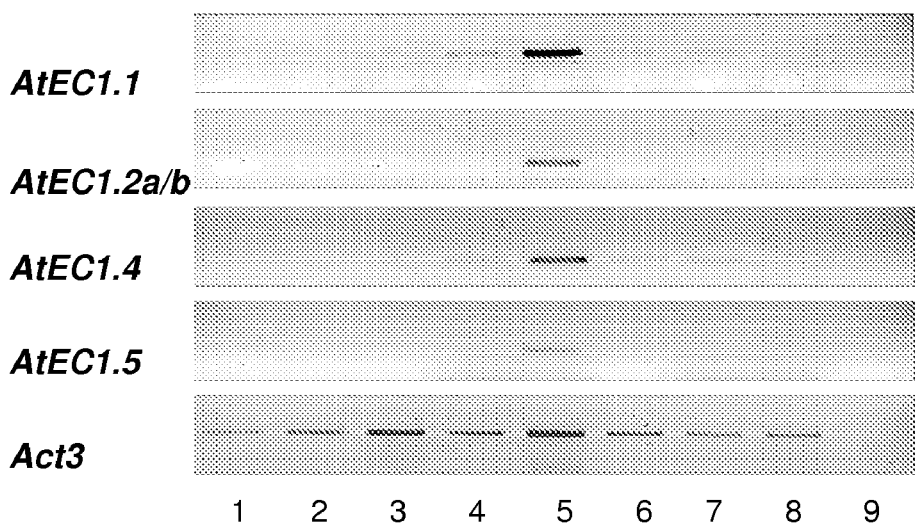
FIG. 2 shows an expression profile of AtEC1-like genes in *Arabidopsis*. Expression was examined by RT-PCR using DNAse treated mRNA from different tissues of *Arabidopsis* and gene specific primers for AtEC1.1, AtEC1.2a/b, AtEC1.4 and AtEC1.5. All five genes of *Arabidopsis* are exclusively expressed in tissues which contain the female gametophyte. Quality and quantity of generated cDNA was verified using primer for the ubiquitously expressed Actin 3 gene. Lane 1: leaf, 2: stem, 3: root, 4: flower bud, 5: mature flower, 6: flower 1-3 dap, 7: pistil, 8: anther, 9: negative control.

The specific expression of TaEC1 was investigated by RT-PCR using DNAse treated total RNA from different tissues of wheat and gene specific primers for the egg cell cDNA cluster C06_3 (TaEC1: SEQ ID NO: 22). Expression of TaEC1 was not detected in any vegetative tissue, in anthers or 12 day old developing caryopsis of wheat. Transcripts were only found in the tissue containing the unfertilized egg cell (pistil), and isolated egg cells. After fertilization, TaEC-1 is down-regulated (see FIG. 1). A similar expression profile was observed for the AtEC1-like genes in Arabidopsis. Expression was examined by RT-PCR using DNAse treated mRNA from different tissues of Arabidopsis and gene specific primers for AtEC1.1, AtEC1.2a/b, AtEC1.4 and AtEC1.5. All five genes of Arabidopsis are exclusively expressed in tissues containing the female gametophyte (see FIG. 2).

EXAMPLE 2

Confirmation of Egg-Cell Specific Expression for AtEC1-Like Transcripts

Figure 3:
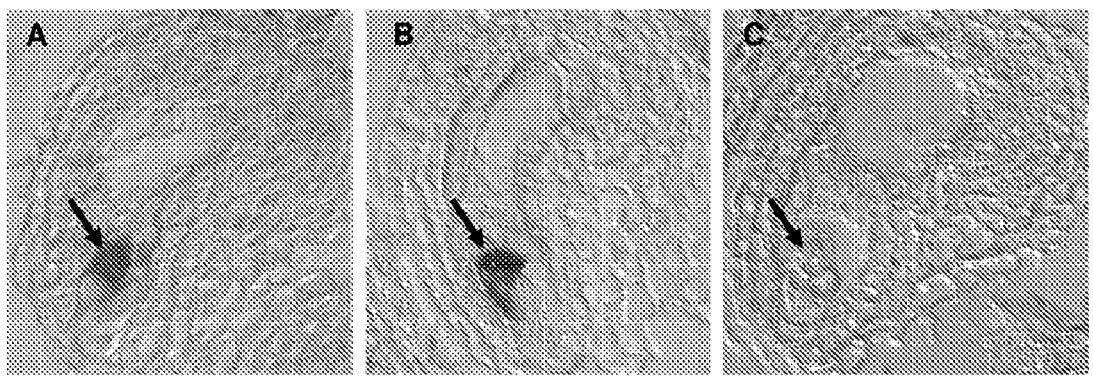
FIG. 3 shows transcript localisation of AtEC1-like genes in *Arabidopsis* ovules. In situ hybridization was performed using embedded sections of mature pistils hybridized with an AtEC1.2a antisense probe (A) and AtEC1.1 antisense probe (B). As control, sense probes of AtEC1.1 (C) and AtEC1.2a were used. Arrows point towards egg cell, showing egg cell specific signals in (A) and (B). Transcripts of AtEC1-like genes could not be detected in other cells of the unfertilized embryo sac or in young embryos, early after fertilization (not shown).

Egg cell-specificity of AtEC1-like transcripts was confirmed by in situ hybridization using embedded sections of mature Arabidopsis pistils hybridized with an AtEC1.2a and AtEC1.1 antisense probe, respectively. As shown in FIG. 3, no mRNA of AtEC1-like genes could be detected in other cells of the unfertilized embryo sac or in young embryos after fertilization.

EXAMPLE 3

Specificity of EC1-Derived Promoters

Figure 4:
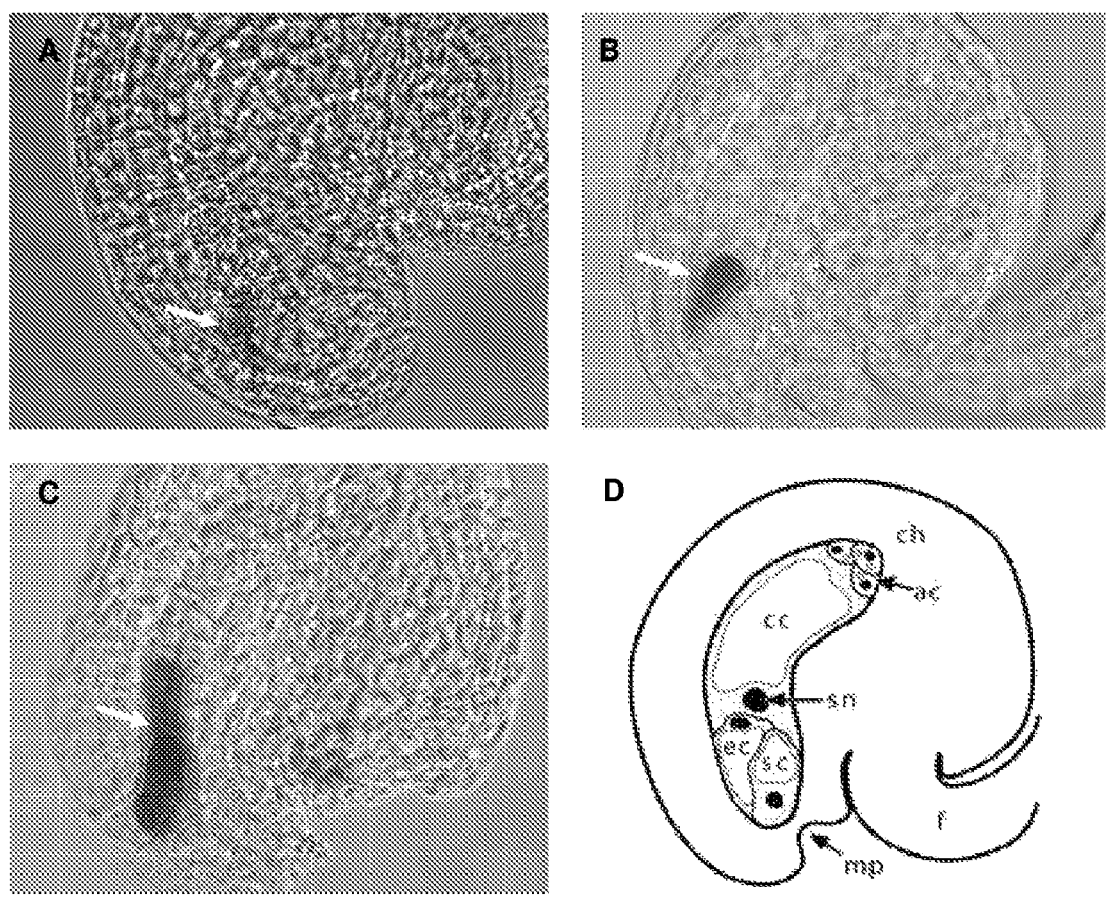
FIG. 4 shows promoter activity of AtEC1-like genes in *Arabidopsis*. Promoters pAtEc1.1 and pAtEc1.2 were cloned as translational fusions 5' upstream of the β-Glucuronidase gene. Cloned constructs were used for stable transformation of *Arabidopsis*. Arrows point at egg cells showing GUS staining in pAtEc1.1::GUS (A) and pAtEc1.2a::GUS ovules before fertilization (B) and a zygote after fertilization (C). GUS activity was only observed in egg cells of unfertilized ovules. After fertilization, GUS activity was still visible in the zygote (C); however, this was due to the high stability of β-Glucuronidase. A schematic of an unfertilized *Arabidopsis* ovule is shown in (D) (Drews and Yadegari, *Annu. Rev. Genet.* 36: 99-124, 2002). Abbreviations: (ac) antipodal cells; (cc) central cell; (ch) chalaza; (ec) egg cell; (emb) embryo; (f) funiculus; (mp) micropyle; (sc) synergid; (sn) secondary nucleus; (zyg) zygote.

Promoter specificity of AtEC1-like genes was analyzed by cloning a defined 5' upstream region of AtEC1.1 (pAtEC1.1: SEQ ID NO: 24) and a defined 5' upstream region of AtEC1.2 (pAtEC1.2: SEQ ID NO: 25) upstream of the β-Glucuronidase (GUS) gene. Cloned constructs were used for stable transformation of Arabidopsis. GUS activity was detected in egg cells of unfertilized ovules. After fertilization, however, GUS activity was still visible in the zygote, due to the high stability of β-Glucuronidase (see FIG. 4).

Figure 5:
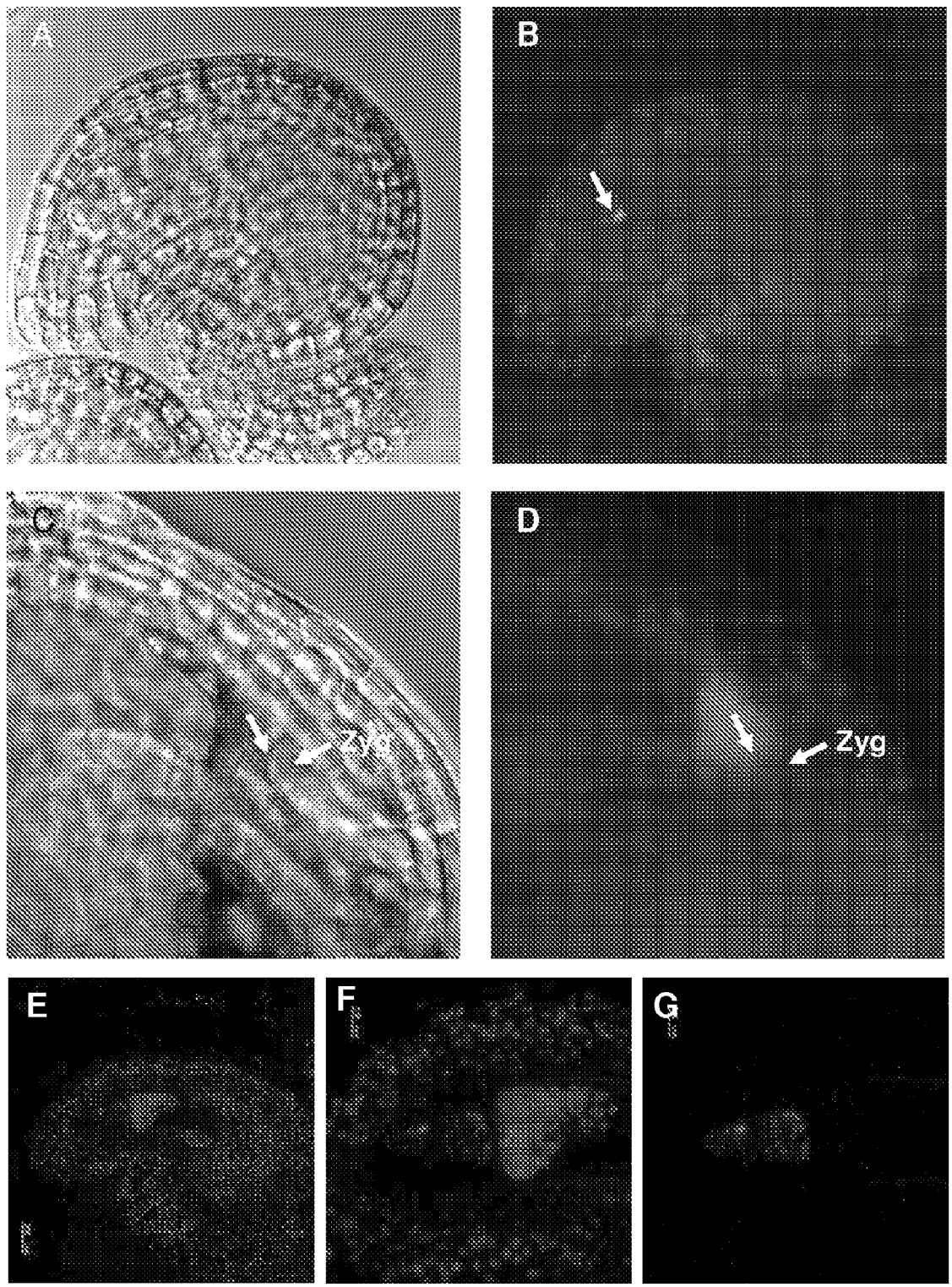
FIG. 5 shows the expression of EGFP (enhanced green fluorescent protein) as a C-terminal fusion to the open reading frame of AtEC1.1, under control of the promoter of pAtEC1.1. The construct was used for transformation of *Ara-* bidopsis thaliana. Ovules of transgenic plants were analyzed microscopically for green fluorescence using DIC (A, C) and UV-light (B, D) as well as UV-light for CLSM (confocal laser scanning microscopy) (E-G). Green fluorescence was visible at the chalazal pole of egg cells in unfertilized ovules (arrow in B) before fertilization. After fertilization, secreted fluorescent protein is visible between the zygote (zyg; arrow) and the neighbouring endosperm (C and D). CLSM shows the protein within vesicles of the unfertilized egg cell. (F) is an enlargement of (E) and (G) shows EGFP fluorescence of the egg cell. Red fluorescence was removed.

In addition, EGFP (enhanced green fluorescence protein) was C-terminal fused to the open reading frame of AtEC1.1 (SEQ ID NO: 13), under control of the AtEC1.1 promoter (SEQ ID NO: 24). The construct was used for transformation of Arabidopsis. Ovules of transgenic plants were analyzed microscopically for green fluorescence under DIC and UV-light. In addition, EGFP signals were observed by Confocal Laser Scanning Microscopy (CLSM). A shown in FIG. 5, green fluorescence was visible exclusively in egg cells of unfertilized ovules. Early after fertilization, some fluorescent protein was still visible in the zygote as well as secreted between the zygote and the neighbouring endosperm. No EGFP could be detected in other cells of the embryo sac or in later stages of embryo development.

EXAMPLE 4

Materials and Methods—Isolation of Wheat Embryo Sac Cells Before and After Fertilization Spikes of Triticum aestivum cv 'Florida' were emasculated 2-4 days before antithesis and covered with bags to prevent fertilization. Egg cells were isolated mechanically from microdissected ovules in 0.55 M sterile mannitol using fine-tipped glass needles and an inverted microscope, as described by Kumlehn et al. (Protoplasma 208: 156-162, 1999). Single cells were transferred into 0.5 ml reaction tubes by using a glass capillary interfaced with a hydraulic system to a micropump. Collected cells were immediately frozen in liquid nitrogen.

EXAMPLE 5

Materials and Methods—mRNA Isolation and cDNA Synthesis mRNA was isolated from 12 egg cells using the Dynabeads® mRNA DIRECT™ Micro kit (Dynal) following the manufacturer's guidelines, but scaled down to 50 µl. Annealed mRNA was isolated using a magnetic particle transfer device (PickPen™, Bio-Nobile). Subsequently, the SMART™ PCR cDNA synthesis kit (BD Biosciences) was used for cDNA synthesis. First-strand cDNA, long distance-PCR, and determination of optimal cycle numbers for generating a population of representative cDNAs was performed according to the manufacturer's guidelines, but using a digoxigenin-11-dUTP (Roche Applied Science) labeled fragment of wheat GAPDH as a probe.

EXAMPLE 6

Materials and Methods—Library Construction and Sequencing

150 µl of cDNA was used for polishing, according to instructions of the SMART™ PCR cDNA synthesis kit (BD Biosciences). Subsequently, 3 µg of EcoRI (NotI) adapters (Invitrogen) were ligated to blunt-end cDNA, using T4 ligase (New England Biolabs). Remaining adapters and fragments below 0.3 kb were removed by electrophoresis in 0.8% low-melting point agarose (Seaplaque GTG). Afterwards, cDNA was extracted using β-agarase I (New England Biolabs). After phosphorylation of EcoRI cohesive ends (10 U/µl T4 polynucleotide kinase, New England Biolabs), a second purification step using Chromaspin™ columns (BD Biosciences) was performed. The cDNA was then ligated into predigested lambda ZAP® II/EcoRI/CIAP vector (Stratagene). The titre of the unamplified library was $1.43 \times 10^6$ pfu/ml. After amplification and in vivo excision, clones were randomly picked and used to generate ESTs. Insert sizes ranged from 300 to 3000 bp, with an average of 900 bp. The average readable sequence length of ESTs was about 500 bp. DNA sequencer trace data subsequently passed an automated cleanup pipeline including PHRED to call bases and assign quality values, followed by CROSS_MATCH to align sequences and to eliminate vector sequences.

EXAMPLE 7

Materials and Methods—Bioinformatics

The sequences were clustered using blastclust (NCBI) and assembled into contigs using Vector NTI 8 (Invitrogen software package). The contig's consensus sequence or the longest representative was used for BLASTN searches against NCBI's nonredundant (nr) database and the EST-database, and for BLASTX searches against NCBI's nr database and SWISSPROT (March 2004). A number of cDNAs resulted in limited sequence information (100-250 bp) from non-coding regions. Therefore, BLASTN searches against the TIGR Wheat Gene Index Release 8.0 (Quackenbush et al., Nucleic Acids Res 29: 159-164, 2001) were performed, using the BLASTN algorithm. If a match with >95% sequence identity over the total length of the query sequence was found, the matching sequence was retrieved and used in subsequent BLASTX searches in place of the original EST. A sequence was considered novel if it did not show a significant match with a sequence of the NCBI databases (nr, EST) or to the TIGR assembled wheat consensus sequences using the BLASTN algorithm (Altschul et al., 1997, supra). The significance threshold used for BLASTN searches were: Score>115, Expect-value<$e^{-25}$.

For BLASTX searches, the cutoff for a significant match for all but the short sequences was an e-value of <$e^{-15}$, Score>=80. Matches to short query sequences (below 260 bp) were inspected and categorized manually. Clusters encoding proteins of known function were manually categorized into broad functional groups using the MIPS (Munich Information Centre for Protein Sequences) classification as guidance.

EXAMPLE 8

Materials and Methods—Expression Analysis by RT-PCR

Wheat RNA was isolated from vegetative and generative tissues using TRIzol® reagent (Invitrogen), essentially following the manufacturer's protocol. Starch containing tissues such as caryopsis were extracted twice, using 3 ml of TRIzol® reagent per 100 mg of tissue. The quality of the total RNA preparation was analyzed by denaturing agarose gel electrophoresis. Before RT-PCR, 1 µg of total RNA was digested with DNAse (RNAse free; Invitrogen) and subsequently used for first-strand cDNA synthesis using Oligo(dT)$_{23}$ (SEQ ID NO:72) (Sigma) and Superscript II reverse transcriptase (Invitrogen), following the manufacturer's protocol but adding RNAseOUT™ (Invitrogen). Quality and amount of generated cDNAs was analyzed by PCR with the following intron-spanning primers directed against wheat GAPDH:

```
TaGAP1 5'-AGGGTGGTGCCAAGAAGGTCA-3'    (SEQ ID NO: 34)

TaGAP2 5'-TATCCCCACTCGTTGTCGTA-3'    (SEQ ID NO: 35)
```

Expression of TaEC1 was analyzed using the primer pair:

```
TaEC1fw2
5'-CCGAGCGGCTGCAGGGAGTGG-3'    (SEQ ID NO: 36)

TaEC1rev2
5'-GCGTCGGAGTAGCCCTTGAGCA-3'   (SEQ ID NO: 37)
```

PCR reactions were carried out for 30 cycles (GAPDH) and 38 cycles (TaEC1) respectively, using 2.5 μl of cDNA as template.

Arabidopsis mRNA was isolated from up to 5 mg tissue using the Dynabeads® mRNA DIRECT™ Micro kit (Dynal) following the manufacturer's guidelines. Annealed mRNA was isolated using a magnetic particle transfer device (PickPen™, Bio-Nobile). Before RT-PCR, the annealed mRNA was treated with DNAse (RNAse free; Invitrogen) in a volume of 10 μl. First-strand cDNA synthesis was carried out using Oligo(dT)$_{20}$ (SEQ ID NO:73) (Invitrogen) and Superscript II reverse transcriptase (Invitrogen), following the manufacturer's protocol but adding RNAseOUT™ (Invitrogen). Quality and amount of generated cDNAs was analyzed by PCR with the following intron-spanning primers directed against Arabidopsis Actin (At2g37620):

```
Act3fw
5'-GATTTGGCATCACACTTTCTACAATG-3'    (SEQ ID NO: 38)

Act3rev
5'-GTTCCACCACTGAGCACAATG-3'    (SEQ ID NO: 39)
```

AtEC1-like cDNAs were amplified using the following gene specific primer pairs for each of AtEC1.1, AtEC1.2a/b, AtEC1.4 and AtEC1.5:

```
AtEC1.1fw
5'-ACAGTGACAGCTCGCCCTCTC-3'    (SEQ ID NO: 40)

AtEC1.1rev
5'-AGTCATTGCCATCATAGTAACCTT-3'    (SEQ ID NO: 41)

AtEC1.2a/bfw
5'-AGTTTCCTCTTTGCCACCATC-3'    (SEQ ID NO: 42)

AtEC1.2a/brev
5'-CACCGTTGAGGAAGAAGAGAA-3'    (SEQ ID NO: 43)

AtEC1.4fw
5'-CCAGCGGAGTCATCAACCAACATA-3'    (SEQ ID NO: 44)

AtEC1.4rev
5'-GGAGACGGAGCCGGAGAAGAGT-3'    (SEQ ID NO: 45)

AtEC1.5fw
5'-GCGCCGGAAACTTGATGGACT-3'    (SEQ ID NO: 46)

AtEC1.5rev
5'-GGCGCCGGTGAAGGAGATAAT-3'    (SEQ ID NO: 47)
```

2 μl of cDNA was used as template for each PCR reaction.

EXAMPLE 9

Materials and Methods—Cloning of Promoter-GUS Fusion Constructs

Genomic DNA of A. thaliana (ecotype Columbia-0) was isolated according to Li and Chory, in *Methods in Molecular Biology* (Vol. 82) Eds. Martínez-Zapater, and Salinas, pp 55-60, 1997). Genomic fragments of AtEC1.1 and AtEC1.2a were amplified from genomic DNA by PCR, using "proofreading" Taq DNA Polymerase (MBI Fermentas). Promoter primer:

```
pAtEC1.1
5'-TGCCTTATGATTTCTTCGGTTTC-3'    (SEQ ID NO: 48)
``` and gene specific primer:

```
AtEC1.1rev1
5'-TCAGAGTCATTGCCATCACAGTAACCTT-3'    (SEQ ID NO: 49)
``` were used for amplification of the promoter region and part of AtEC1.1 gene (837 bp). Promoter primer:

```
pAtEC1.2a
5'- AAGCATTTGCGTTTGGTTTATC-3'    (SEQ ID NO: 50)
``` and terminator primer:

```
tAtEC1.2a
5'- AATGCGGTTTTAGTCACACG-3'    (SEQ ID NO: 51)
``` were used for amplification of AtEC1.2a (1371 bp). Genomic amplification products were cloned into pCR®2.1-TOPO® (Invitrogen), after adding 3' adenines (TOPO-gAtEC1.1 and TOPO-gAtEC1.2a). 3'A-addition, ligation and transformation of competent TOP10F' cells was performed according the manufacturer's guidelines.

Gene specific primers containing restriction sites were designed to clone the promoters in front of the β-glucuronidase gene (uidA; Jefferson et al. *EMBO J.* 6: 3901-3907, 1987). 457 bp 5' upstream of the AtEC1.1 start codon was amplified from TOPO-gAtEC1.1 using the primers M13rev (vector primer) and:

```
AtEC1.1-PstI
5'-CCATTTCTCTGCAGATTGATAA-3'    (SEQ ID NO: 52)
```

893 bp 5' upstream of the AtEC1.2a start codon was amplified from TOPO-gAtEC1.2a using the primers M13rev (vector primer) and:

```
AtEC1.2a-BgIII
5'-CCATAGATCTTTCTTTTTGGGG-3'    (SEQ ID NO: 53)
```

After precipitation of PCR reactions (1/10 vol. 3M NaAc, pH 5.2/1 vol. Isopropanol), the purified fragments were restricted with PstI (AtEC1.1 promoter) and BamHI/BgIII (AtEC1.2a promoter), respectively. The same enzymes were used for restriction of the GUS containing vector pMG2002 (Manfred Gahrtz, unpublished), thereby removing the maize ubiquitin promoter in front of the GUS gene. Restricted fragments and vectors were purified using the "Easy Pure" DNA purification kit (Biozym). Before ligation, PstI and BamHI/BgIII digested plasmids were dephosphorylated using CIAP (Calf Intestine Alkaline Phosphatase; MBI Fermentas), following the manufacturer's guidelines. Promoters were ligated into digested and dephosphorylated vectors using T4 ligase (1 U/μl; Invitrogen), following the manufacturer's protocol. Ligation reactions were used for transforming competent Top10F' cells (Invitrogen). Positive clones were selected by colony PCR, using gene specific primers:

```
Gus start rev
5'-ATCCAGACTGAATGCCCACA-3',    (SEQ ID NO: 54)

pAtEC1.1                       (SEQ ID NO: 48)
and pAtEC1.2a.                     (SEQ ID No: 50)
```

All plasmid preparations were performed either using the E.Z.N.A. Plasmid Miniprep Kit II (Peqlab), or the QIAGEN plasmid Midi Kit 100 (Qiagen). All cloned fragments and constructs were verified by sequencing, using either flanking primers M13fw and M13rev (TOPO-gAtEC1.1 and TOPO-gAtEC1.2a), or the gene specific primers GUS Start rev (SEQ ID NO: 54), pAtEC1.1 (SEQ ID NO: 48) and pAtEC1.2a (SEQ ID NO: 50).

EXAMPLE 10

Materials and Methods—Cloning of GFP-Fusion Protein

EGFP (enhanced green fluorescence protein; Pang et al. *Plant Physiol* 112: 893-900, 1996) was C-terminal fused to the open reading frame of AtEC1.1, under control of the AtEC1.1 promoter. The promoter and open reading frame of AtEC1.1 was amplified from genomic DNA using "proof reading" Taq polymerase (MBI Fermentas) and the primers:

```
E1F   5'-GCCTTATGATTTCTTCGGTT-3'    (SEQ ID NO: 55)

E1R   5'-GCAGGAGTGTAAAGATGAAT-3'    (SEQ ID NO: 56)
```

A second amplification of AtEC1.1 was performed using the modified primers:

```
EC1-PF2
5'-CCCCGAATTCCTTATGATTTCTTCGGT-3'    (SEQ ID NO: 57)

EC1-R
5'-CTCGGATCCGGGTTAGAAGGAGAA-3.       (SEQ ID NO: 58)
```

After restriction with EcoRI and BamHI, the fragment was cloned into the EcoRI-BamHI sites of the vector p7U-GFP (DNA Cloning Service). The C-terminal fusion of EGFP and the sequence of cloned fragment was verified by sequencing using the primers:

```
GFP-seq   5'-CCAGTTCCACCAGGATTG-3'   (SEQ ID NO: 59)

LH1       5'-CCCAAGATCTGGCCCTT-3'.   (SEQ ID NO: 60)
```

EXAMPLE 11

Materials and Methods—Stable Transformation of *Arabidopsis*

For plant transformation, vectors were transferred into *Agrobacterium tumefaciens* strain GV3101 (Koncz and Schell, *Mol Gen Genet.* 204: 383-396, 1986). Transformations were performed on ecotype Columbia-0 by a "floral dip" procedure according to Clough and Bent (*Plant J* 16: 735-743, 1998). The seeds obtained from the T0 transformants were germinated on soil after a cold-treatment of 2 days at 2° C. Three days after germination, transgenics were selected by spraying 200 mg/l BASTA® (Bayer Crop Science) supplemented with 0.1% Tween. BASTA® treatment was repeated two times after three days, each. Surviving seedlings were transferred to single pots. BASTA® resistant plants of the T1 and T2 generation were analyzed for the presence of the T-DNA by PCR using GUS primers:

```
GUS3   5'-GCGTGGTGATGTGGAGTATTG-3'   (SEQ ID NO: 61)

GUS4   5'-TCACCGAAGTTCATGCCAGTC-3'   (SEQ ID NO: 62)
``` or primers:

```
bar-fw
5'-CCGTACCGAGCCGCAGGAAC-3'           (SEQ ID NO: 63)

bar-rev
5'-CAGATCTCGGTGACGGGCAGGAC-3'        (SEQ ID NO: 64)
```

EXAMPLE 12

Materials and Methods—GUS Staining

Activity of β-glucuronidase (GUS; Jefferson et al., 1987, supra) was performed according to a protocol of Vielle-Calzada et al. (*Nature* 404: 91-94, 2000). Inflorescences, siliques, leaves, and stems from soil-grown plants were transferred to microtiter wells containing 500 µl of GUS staining buffer. Pistils and siliques were cut open lengthwise with a hypodermic needle (0.4×20 mm, Braun) before transferring into GUS staining buffer. Microtiter dishes were placed under vacuum for 5 min. After release of vacuum, plates were covered with a lid and incubated at 37° C. in the dark for 6 hours, or up to 3 days. Afterwards, the solution was removed and the tissues were cleared in 70% ethanol. Ovules were isolated on a glass slide by dissecting the pistils with a syringe in a drop of sodium phosphate buffer, pH 7.0. Ovules were cleared using either Hoyers solution (Liu and Meinke, *Plant J* 16: 21-31, 1998) or Chloral hydrate clearing buffer (80 g Chloral hydrate, 20 ml $H_2O$, 10 ml glycerol) and analyzed under a Zeiss Axioskop microscope under differential interference contrast (DIC) optics. Images were captured on an Axiocam camera (Zeiss) using the Axiovision program AC Release 4.1 (Zeiss).

EXAMPLE 13

Materials and Methods—GUS Staining

Ovules of transgenic *Arabidopsis* plants were dissected on glass slides in phosphate buffered saline, pH 7.4 (8 g NaCl, 0.2 g KCl, 1.44 g $Na_2HPO_4$, 0.24 g $KH_2PO_4$). Fluorescence was observed using a Confocal Laser Scanning Microscope (CLSM), as described by Knebel et al. (*Eur J Cell Biol* 52: 328-340, 1990).

EXAMPLE 14

Materials and Methods—In Situ Hybridization

Non radioactive in situ hybridization with DIG labeled RNA probes of AtEC1.1 and AtEC1.2a was performed as described by Vielle-Calzada (*Genes Dev* 13: 2971-2982, 1999). For generating RNA probes by in vitro transcription, the open reading frame and 3'-UTR of AtEC1.1 and AtEC1.2a was amplified from genomic DNA by PCR and subsequently cloned into pCR®II-TOPO® (Invitrogen).

Primers used for amplification of AtEC1.1 were:

```
1-1fwXbaI
5'-ATCTGTCTAGAAATGGCTTC-3'        (SEQ ID NO: 65)

1-1revXbaI
5'-TTTATTCTAGAAAGTAATAACAG-3'     (SEQ ID NO: 66)
```

Primers used for amplification of AtEC1.2a were:

```
At2a-BglIIfw
5'-AAAGAAAGATCTATGGCTTCTAAC-3'    (SEQ ID NO: 67)

At2a-SaIrev
5'-TCATTAGTCGACTTTGCATACATC-3'    (SEQ ID NO: 68)
```

Ligation of PCR products into pCR®II-TOPO® and transformation of competent cells was performed according the manufacturer's guidelines.

Positive colonies were selected by colony PCR, using the vector primers M13-20 and M13rev. Plasmids were prepared using the QIAGEN plasmid Midi Kit 100 (Qiagen). Cloned fragments were verified by sequencing, using the vector primers M13fw and M13rev. The plasmids were linearized using BamHI (sense) and XhoI (antisense) and purified by two times of phenol/chloroform extractions followed by precipitation. Run off transcripts of linearized plasmids (0.5 µg/µl in DEPC-treated water) were generated by using T7 and SP6 polymerases for in vitro transcription. In situ hybridization of *Arabidopsis* ovules with sense and antisense probes was performed using 8 µm sections of embedded mature unfertilized and fertilized pistils, essentially following a protocol of Jackson, D. (in: *Molecular Plant Pathology, A Practical Approach*. (Bowles, D. J., Gurr, S. J. and McPhereson, M., eds.), Oxford University Press, U.K., 163-174, 1991).

DNA and protein sequences were aligned using ClustalW software (Higgins et al., *Nucl. Acids Res.* 22: 4673-4680, 1994) and alignments drawn by GeneDoc version 2.6.02 (Nicholas et al., *Embnew. News* 4: 14, 1997).

EXAMPLE 15

Detection of Conserved Motifs in EC1-Derived Transcriptional Control Sequences

Each of the EC1-derived transcriptional control sequences defined herein (ie. SEQ ID NO: 24, SEQ ID NO: 25, SEQ ID NO: 26, SEQ ID NO: 27, SEQ ID NO:28, SEQ ID NO: 29, SEQ ID NO: 30, SEQ ID NO: 31, SEQ ID NO: 32) were inspected for known cis-regulatory elements by PLACEdb 26.0 (see the world wide web at dna.affree.go.jp/PLACE/), a database of motifs found in plant cis-acting regulatory DNA elements.

Identification of novel sequence motifs was performed computationally using the sequence analysis software Lasergene/MegAlign (DNASTAR, Inc., 1228 South Park Street, Madison, Wis. 53715, USA).

All of the transcriptional control sequences were aligned pair wise with each other using two algorithms, Martinez Needleman-Wunsch DNA Alignment (Minimum Match: 9; Gap Penalty: 1 0.10; Gap Length Penalty: 0.33) and Wilbur-Lipman DNA Alignment (Ktuple: 3; Gap Penalty: 3; Window: 20). In addition, over-represented motifs in all of the upstream regions of the transcriptional control sequences were analyzed by the motif finding algorithm MotifSampler (Thijs et al., *Journal of Computational Biology*, 9(2), 447-464, 2002) on the internet at homes.esat.kuleuven.be/~thijs/Work/MotifSampler.html (see FIG. 10).

Two motifs were identified in the upstream regions of SEQ ID NO: 24, SEQ ID NO: 25, SEQ ID NO: 26, SEQ ID NO: 27, SEQ ID NO: 28, SEQ ID NO: 30 and SEQ ID NO: 31. The consensus sequences of two novel sequence motifs identified were as follows:

EC1 promoter nucleotide sequence motif #1: 5'-CCAC-TAAT-3' (SEQ ID NO: 33)

EC1 promoter nucleotide sequence motif #2: 5'-kTAATTAm-3' (SEQ ID NO: 69)

As the expression of the subject EC1 genes is regulated in a similar manner, the identified motifs represent putative cis-regulatory elements for egg cell specificity of the transcriptional control sequences.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it must be noted that, as used herein, the singular forms "a", "an" and "the" include plural aspects unless the context already dictates otherwise. Thus, for example, reference to "a nucleotide sequence of interest" includes a single nucleotide sequence as well as two or more nucleotide sequences; "an egg cell" includes a single egg cell as well as two or more egg cells; and so forth.

Future patent applications may be filed in Australia or overseas on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the invention or inventions inherent in the present disclosure. Features may be added to or omitted from the example claims at a later date, so as to further define the invention or inventions.

The invention claimed is:

1. A nucleic acid construct comprising:
a plant female gamete-specific transcriptional control sequence, wherein said transcriptional control sequence comprises (i) the nucleotide sequence set forth in SEQ ID NO: 24, or (ii) a functionally active fragment or variant of (i), said functionally active fragment or variant comprising a nucleotide sequence which is at least 95% identical to SEQ ID NO: 24 over the full length of SEQ ID NO: 24, and wherein said transcriptional control sequence is operably connected to a nucleotide sequence of interest which is heterologous with respect to the transcriptional control sequence and induces expression of the nucleotide sequence of interest in egg cells.

2. An isolated cell comprising the nucleic acid construct according to claim 1; or a genomically integrated form of said construct.

3. The cell according to claim 2, wherein the cell is a plant cell.

4. The cell according to claim 3, wherein the cell is a plant egg cell.

5. The cell according to claim 4, wherein the level, rate and/or pattern of expression of at least one nucleotide sequence is altered in said plant egg cell relative to a wild type form of said plant egg cell.

6. A multicellular plant structure comprising the construct according to claim 1.

7. The multicellular plant structure according to claim 6, wherein the multicellular plant structure comprises a plant part, organ or tissue.

8. The multicellular plant structure according to claim 7, wherein said multicellular plant structure comprises one or more plant egg cells.

9. A method for specifically or preferentially expressing a nucleotide sequence of interest in a plant egg cell, the method comprising introducing the nucleic acid construct according to claim 1 into a plant.

10. The nucleic acid construct according to claim 1 wherein said transcriptional control sequence comprises the nucleotide sequence of SEQ ID NO: 24.

* * * * *

SEQUENCE LISTING

```
<160> NUMBER OF SEQ ID NOS: 74

<210> SEQ ID NO 1
<211> LENGTH: 20
<212> TYPE: PRT
<213> ORGANISM: Artificial Sequence
<220> FEATURE:
<223> OTHER INFORMATION: portion of EC1 transcriptional control sequence
      polypeptide consensus sequence
```

```
<221> NAME/KEY: VARIANT
<222> LOCATION: (3)...(7)
<223> OTHER INFORMATION: Xaa = any amino acid
<221> NAME/KEY: VARIANT
<222> LOCATION: (8)...(8)
<223> OTHER INFORMATION: Xaa = Leu or Ile
<221> NAME/KEY: VARIANT
<222> LOCATION: (9)...(9)
<223> OTHER INFORMATION: Xaa = any amino acid
<221> NAME/KEY: VARIANT
<222> LOCATION: (10)...(10)
<223> OTHER INFORMATION: Xaa = Ser or His
<221> NAME/KEY: VARIANT
<222> LOCATION: (12)...(12)
<223> OTHER INFORMATION: Xaa = Thr or Ser
<221> NAME/KEY: VARIANT
<222> LOCATION: (13)...(13)
<223> OTHER INFORMATION: Xaa = any amino acid
<221> NAME/KEY: VARIANT
<222> LOCATION: (14)...(14)
<223> OTHER INFORMATION: Xaa = Asp or Glu
<221> NAME/KEY: VARIANT
<222> LOCATION: (15)...(15)
<223> OTHER INFORMATION: Xaa = Ile or Leu
<221> NAME/KEY: VARIANT
<222> LOCATION: (16)...(16)
<223> OTHER INFORMATION: Xaa = Ile, Leu or Val
<221> NAME/KEY: VARIANT
<222> LOCATION: (17)...(17)
<223> OTHER INFORMATION: Xaa = any amino acid
<221> NAME/KEY: VARIANT
<222> LOCATION: (20)...(20)
<223> OTHER INFORMATION: Xaa = Leu, Ile or Val

<400> SEQUENCE: 1

Cys Trp Xaa Xaa Xaa Xaa Xaa Xaa Xaa Cys Xaa Xaa Xaa Xaa Xaa
 1               5                  10                  15

Xaa Phe Phe Xaa
            20

<210> SEQ ID NO 2
<211> LENGTH: 158
<212> TYPE: PRT
<213> ORGANISM: Arabidopsis thaliana
<220> FEATURE:
<223> OTHER INFORMATION: AtEC1.1

<400> SEQUENCE: 2

Met Ala Ser Lys Ser Ser Phe Met Ala Thr Phe Asn Ile Val Thr Leu
 1               5                  10                  15

Met Leu Met Val Ala Ser Ser Thr Val Thr Ala Arg Pro Leu Met Lys
            20                  25                  30

Pro Ser Met Gly Thr Ser Ser Pro Thr Thr Ser Leu Val Tyr Arg Leu
        35                  40                  45

Lys Leu Asp Glu Asp Thr Gly Tyr Cys Trp Asp Ser Leu Met Gln Leu
    50                  55                  60

Gln His Cys Ser Gly Glu Leu Ile Leu Phe Phe Leu Asn Gly Glu Thr
65                  70                  75                  80

Tyr Ile Gly Pro Gly Cys Cys Ser Ala Ile Arg Thr Ile Gly Arg Lys
                85                  90                  95

Cys Trp Pro Thr Met Ile Gly Val Leu Gly Phe Thr Ala Gln Glu Gly
            100                 105                 110

Asp Met Leu Gln Gly Tyr Cys Asp Gly Asn Asp Ser Asn Asn Gly
        115                 120                 125

Glu Asp His Ala Leu Ala Ser Ser Thr Leu Pro Leu Ser Val Asn Phe
    130                 135                 140

Lys Thr Thr Val Val Arg Ser Ser Ala Ser Pro Ser Asn Pro
```

```
                 145                 150                 155

<210> SEQ ID NO 3
<211> LENGTH: 125
<212> TYPE: PRT
<213> ORGANISM: Arabidopsis thaliana
<220> FEATURE:
<223> OTHER INFORMATION: AtEC1.2a

<400> SEQUENCE: 3

Met Ala Ser Asn Thr Ser Phe Leu Phe Ala Thr Ile Ala Ile Leu Leu
  1               5                  10                  15

Val Leu Asn Ile Ser Gly Arg Thr Leu Pro Glu Thr Glu Asp Ser Thr
             20                  25                  30

Asn Ile Ala Ala Arg Leu Asn Gly Gly Gly Leu Met Glu Cys Trp Asn
         35                  40                  45

Ala Leu Tyr Glu Leu Lys Ser Cys Thr Asn Glu Ile Val Leu Phe Phe
     50                  55                  60

Leu Asn Gly Glu Thr Lys Leu Gly Val Asp Cys Gln Ala Val Glu
 65                  70                  75                  80

Val Ile Thr Thr Asp Cys Trp Pro Ala Met Leu Thr Ser Leu Gly Phe
                 85                  90                  95

Thr Ser Asp Glu Thr Asn Val Leu Arg Gly Phe Cys Gln Ser Pro Asn
            100                 105                 110

Ser Gly Gly Ser Ser Pro Ala Pro Ser Ser Val Lys Leu
        115                 120                 125

<210> SEQ ID NO 4
<211> LENGTH: 125
<212> TYPE: PRT
<213> ORGANISM: Arabidopsis thaliana
<220> FEATURE:
<223> OTHER INFORMATION: AtEC1.2b

<400> SEQUENCE: 4

Met Ala Ser Asn Thr Ser Phe Leu Phe Val Thr Val Thr Leu Leu Leu
  1               5                  10                  15

Val Leu Asn Val Ser Ser Arg Ala Leu Pro Pro Val Ala Asp Ser Thr
             20                  25                  30

Asn Ile Ala Ala Arg Leu Thr Gly Gly Gly Leu Met Gln Cys Trp Asp
         35                  40                  45

Ala Leu Tyr Glu Leu Lys Ser Cys Thr Asn Glu Ile Val Leu Phe Phe
     50                  55                  60

Leu Asn Gly Glu Thr Lys Leu Gly Tyr Gly Cys Asn Ala Val Asp
 65                  70                  75                  80

Val Ile Thr Thr Asp Cys Trp Pro Ala Met Leu Thr Ser Leu Gly Phe
                 85                  90                  95

Thr Leu Glu Glu Thr Asn Val Leu Arg Gly Phe Cys Gln Ser Pro Asn
            100                 105                 110

Ser Gly Gly Ser Ser Pro Ala Leu Ser Pro Val Lys Leu
        115                 120                 125

<210> SEQ ID NO 5
<211> LENGTH: 127
<212> TYPE: PRT
<213> ORGANISM: Arabidopsis thaliana
<220> FEATURE:
<223> OTHER INFORMATION: AtEC1.4

<400> SEQUENCE: 5
```

```
Met Ala Ser Asn Thr Thr Phe Leu Phe Ser Thr Val Thr Leu Leu Ile
1               5                   10                  15

Ile Leu Leu Asn Thr Thr Val Ser Gly Arg Asp Leu Pro Ala Glu Ser
            20                  25                  30

Ser Thr Asn Ile Ala Ala Arg Leu Gln Ser Gly Gly Leu Met Glu Cys
            35                  40                  45

Trp Asn Ala Leu Tyr Glu Leu Lys Ser Cys Thr Asn Glu Ile Val Leu
        50                  55                  60

Phe Phe Leu Asn Gly Glu Thr Lys Leu Gly Val Ser Cys Cys Glu Ser
65                  70                  75                  80

Val Asp Ile Ile Thr Thr Asn Cys Trp Pro Ala Met Leu Thr Ser Leu
                85                  90                  95

Gly Phe Thr Pro Glu Glu Ala Asn Val Leu Arg Gly Phe Cys Gln Asn
            100                 105                 110

Pro Asn Ser Gly Asp Ser Ser Pro Ala Pro Ser Pro Lys Ile Val
            115                 120                 125
```

<210> SEQ ID NO 6
<211> LENGTH: 155
<212> TYPE: PRT
<213> ORGANISM: Arabidopsis thaliana
<220> FEATURE:
<223> OTHER INFORMATION: AtEC1.5

<400> SEQUENCE: 6

```
Met Ala Thr Lys Ser Thr Ser Lys Pro Leu Leu Leu Ser Phe Leu Met
1               5                   10                  15

Met Ser Tyr Leu Ile Ser Thr Phe His Val Ile Thr Val Ala Glu Gly
            20                  25                  30

Arg Thr Leu Gln Phe Thr Lys Met Ala Thr Asp His Ser Gly Ala Gly
            35                  40                  45

Asn Leu Met Asp Cys Trp Asn Ala Gly Leu Glu Leu Lys Ser Cys Thr
        50                  55                  60

Asp Glu Ile Val Lys Phe Phe Leu Ser Gln Thr Gly Thr Ser Glu Pro
65                  70                  75                  80

Pro Val Lys Gly Gly Ile Asp Lys Asp Cys Cys Gly Ala Ile Gly Leu
            85                  90                  95

Val Val Lys Asp Cys Trp Ser Val Met Phe Thr Ser Leu Gly Leu Thr
            100                 105                 110

Thr Met Glu Gly Asn Asn Leu Arg Glu Tyr Cys Glu Phe Gln Ala Glu
            115                 120                 125

Lys Ser Glu Leu Ser Pro Ser Pro Ala Pro Glu Thr Leu Ala Leu Ser
            130                 135                 140

Pro Val Glu Ile Thr Tyr Pro Gly Leu Asp Tyr
145                 150                 155
```

<210> SEQ ID NO 7
<211> LENGTH: 133
<212> TYPE: PRT
<213> ORGANISM: Medicago truncatula
<220> FEATURE:
<223> OTHER INFORMATION: MtEC1.1

<400> SEQUENCE: 7

```
Met Ala Phe Phe Leu Lys Leu Phe Ile Ile Ser Leu Ser Thr Ile
1               5                   10                  15

Val Thr Ala Thr Ser Leu Ser Ser Thr Lys Thr Leu Ala Ser Arg Leu
            20                  25                  30
```

```
Glu Leu Phe Asp Gly Ser Gly Pro Asn Asn Lys Cys Trp Glu Thr Met
         35                  40                  45

Leu Glu Leu Gln His Cys Thr Gly Asp Ile Val Thr Phe Phe Leu Asn
 50                  55                  60

Gly Gln Thr His Leu Gly Ser Gly Cys Cys Asn Ala Leu Leu Thr Ile
 65                  70                  75                  80

Ala Gln Glu Cys Trp Gly Asn Leu Leu Thr Ser Leu Gly Leu Thr Val
                 85                  90                  95

Glu Glu Ala Glu Ile Leu Arg Gly Phe Cys Ala Arg Val Ala Ser Val
                100                 105                 110

Asn Asn Ser Leu Leu Pro Ser Ile Thr Val Asp Ala Pro Ser Pro Ala
            115                 120                 125

Pro Ile Asn Asn Tyr
        130

<210> SEQ ID NO 8
<211> LENGTH: 151
<212> TYPE: PRT
<213> ORGANISM: Oryza sativa
<220> FEATURE:
<223> OTHER INFORMATION: OsEC1.1

<400> SEQUENCE: 8

Met Ala Cys Ser Gly Ser Phe Leu Pro Ile Met Leu Leu Pro Leu Leu
 1               5                  10                  15

Leu Ala Gly Ala Ala Val Ala Gly Gly Ala Pro Pro Gly Leu Gly Leu
                 20                  25                  30

Ala Gln Arg Leu Ala Asp Gly Val Gly Gln Gln Gln Gln Cys Trp
             35                  40                  45

Glu Val Leu Met Glu Ile Lys Ser Cys Thr Gly Glu Ile Leu Leu Phe
 50                  55                  60

Phe Ile Asn Gly Glu Ala Tyr Leu Gly Pro Gly Cys Cys Arg Ala Ile
 65                  70                  75                  80

Arg Val Ile Glu Gln Ser Cys Trp Ala Thr Asp Ala Met Leu Ser Val
                 85                  90                  95

Ile Gly Phe Thr Pro Glu Glu Gly Asp Met Leu Lys Gly Tyr Cys Asp
                100                 105                 110

Ala Gly Asp Glu His Lys Pro Ser Pro Pro Ala Ser Pro Ala Val
            115                 120                 125

Gly Tyr Val Ala Val Gly Glu Asn Ala Ala Val Pro Ala Gly Arg Lys
130                 135                 140

Ser Leu Ala Leu Gln His Arg
145                 150

<210> SEQ ID NO 9
<211> LENGTH: 139
<212> TYPE: PRT
<213> ORGANISM: Oryza sativa
<220> FEATURE:
<223> OTHER INFORMATION: OsEC1.2

<400> SEQUENCE: 9

Met Ala Ser Leu Leu Ser Val Ala Val Val Leu Val Val Val Ser Ala
 1               5                  10                  15

Gln Ala Leu Ala Ala Val Ala Val Asp Ala Ala Arg Val Asn Ala
             20                  25                  30

Gly Ala Ala Ala Phe Ser Pro Ala Val Pro Leu Gly Gly Arg Leu Asp
             35                  40                  45
```

```
Gly Gly Gly Gly Gly Leu Val Glu Cys Trp Ser Ala Val Ala Glu Leu
 50                  55                  60

Arg Ser Cys Thr Asp Glu Ile Val Leu Phe Phe Leu Asn Gly Glu Thr
 65                  70                  75                  80

Thr Gln Leu Gly Ala Gly Cys Cys Arg Ala Val Arg Ala Ala Thr Arg
                 85                  90                  95

Asp Cys Trp Pro Ala Met Leu Ala Ala Val Gly Phe Thr Ala Glu Glu
                100                 105                 110

Ala Asp Val Leu Arg Gly Leu Cys Asp Ala Glu Ala Ala Ala Ala Ala
                115                 120                 125

Ala Asp Ser Thr Ser Pro Ala Pro Ser Ala Ala
            130                 135

<210> SEQ ID NO 10
<211> LENGTH: 144
<212> TYPE: PRT
<213> ORGANISM: Oryza sativa
<220> FEATURE:
<223> OTHER INFORMATION: OsEC1.3

<400> SEQUENCE: 10

Met Ala Leu Ala Val Lys Leu Ala Val Leu Leu Leu Ala Ala Ala
  1               5                  10                  15

Ala Ala Gly Gly Ser Ser Thr Thr Thr Val Pro Pro Leu Glu Glu Arg
                 20                  25                  30

Leu Gly Ala Ala Phe Asp Gly Met Ala Ala Ala Glu Gly Gly Gly
             35                  40                  45

Gly Gly Gly Trp Met Met Glu Cys Trp Ser Ala Val Thr Lys Leu Gly
 50                  55                  60

Ser Cys Thr Asn Glu Ile Val Leu Phe Phe Val Asn Gly Glu Ser Tyr
 65                  70                  75                  80

Leu Gly Pro Asp Cys Cys Val Ala Ile Arg Thr Val Thr Arg Arg Cys
                 85                  90                  95

Trp Pro Ala Met Leu Ala Ser Ile Gly Phe Thr Ala Gln Glu Ala Asp
                100                 105                 110

Ile Leu Arg Gly Phe Cys Asp Ala Glu Leu Ala Ala Pro Pro Pro
                115                 120                 125

Ser Thr Asn Ala Ser Ser Ala Pro Ala Pro Ala Pro Ala Ser Ala
            130                 135                 140

<210> SEQ ID NO 11
<211> LENGTH: 151
<212> TYPE: PRT
<213> ORGANISM: Triticum aestivum
<220> FEATURE:
<223> OTHER INFORMATION: TaEC1

<400> SEQUENCE: 11

Met Ala Ser Ser Gly Ser Leu Leu Pro Ala Leu Leu Val Leu Leu Leu
  1               5                  10                  15

Leu Thr Val Ala Ala Thr Ala Ser Thr Thr Thr Thr Phe Val Arg
             20                  25                  30

Ala Gly Ala Pro Pro Ala Glu Leu Ala Glu Arg Leu Gln Gly Val Gly
             35                  40                  45

Gln Gln Gln Cys Trp Glu Ile Leu Met Asp Ile Arg Ser Cys Thr Gly
 50                  55                  60

Glu Ile Ile Leu Phe Phe Leu Asn Gly Glu Ala Tyr Leu Gly Pro Gly
 65                  70                  75                  80
```

```
Cys Cys Arg Ala Ile Arg Ala Val Glu Gln His Cys Trp Ala Ala Asp
                85                  90                  95

Ala Thr Leu Ser Val Ile Gly Phe Thr Pro Glu Glu Gly Asp Met Leu
            100                 105                 110

Lys Gly Tyr Cys Asp Ala Gly Asp Ser Gly Glu Gly Gln Gln Arg Gly
        115                 120                 125

Ala Phe Asp Gly Val Ala Ser Asp Gly Ala Val Ala Ala Ala Ala Gly
    130                 135                 140

Arg Lys Gly Leu Gly Ala Pro
145                 150

<210> SEQ ID NO 12
<211> LENGTH: 174
<212> TYPE: PRT
<213> ORGANISM: Hordeum vulgare
<220> FEATURE:
<223> OTHER INFORMATION: HvECA1

<400> SEQUENCE: 12

Met Ala Ser Ser Gly Pro Leu Leu Pro Thr Leu Leu Val Leu Leu Ala
1               5                   10                  15

Ala Ala Ala Ala Thr Ala Ser Ala Ala Gly Ala Arg Pro Ala Ser Thr
                20                  25                  30

Thr Thr Ala Thr Thr Phe Val Arg Ala Ala Asp Leu Ala Asp Arg Leu
            35                  40                  45

Glu Gly Ala Val Ser Gln Gln Cys Trp Glu Thr Leu Leu His Ile Lys
        50                  55                  60

Ser Cys Thr Gly Glu Ile Ile Leu Phe Phe Leu Asn Gly Glu Ala Tyr
65                  70                  75                  80

Leu Gly Pro Gly Cys Cys Arg Ala Ile Arg Ala Ile Glu Gln Arg Cys
                85                  90                  95

Trp Ala Ala Asp Leu Met Leu Ser Val Ile Gly Phe Thr Pro Glu Glu
            100                 105                 110

Gly Asp Met Leu Lys Gly Tyr Cys Asp Ala Gly Asp Asp Asp Asn Asn
        115                 120                 125

Asn Gly Pro Arg His Ser Phe Gly Gly Ser Ser Pro Ala Pro Pro Pro
    130                 135                 140

Arg Arg Ala Leu Gly Ala Asp Gly Val Ala Thr Gly Ala Gly Thr Val
145                 150                 155                 160

Ala Ala Ala Ala Gly Arg Lys Gly Leu Gly Ala Pro Val Gly
                165                 170

<210> SEQ ID NO 13
<211> LENGTH: 477
<212> TYPE: DNA
<213> ORGANISM: Arabidopsis thaliana
<220> FEATURE:
<223> OTHER INFORMATION: AtEC1.1 transcriptional control sequence open
      reading frame (ORF)

<400> SEQUENCE: 13
atggcttcca aatctagttt catggctacc ttcaacattg tgactctcat gctcatggtg     60
gcttcctcca cagtgacagc tcgccctctc atgaaaccat ccatgggac gtcttctcct    120 accacaagcc ttgtgtacag gctcaagctt gatgaagata cagggtactg ctgggactca    180
ctgatgcagc tccaacactg ttctggagag ctgatcttgt tcttcctcaa cggtgagact    240
tacattggcc ctgggtgttg cagtgctata agaaccattg acgcaagtg ttggcctact    300 atgattggtg tcttggtttt tactgctcaa gaaggtgata tgctccaagg ttactgtgat    360
```

```
ggcaatgact ctgacaacaa tggtgaagac catgctcttg cctcctcaac actgcctctc    420
tccgtgaatt tcaagactac cgttgttaga tcttctgctt ctccttctaa cccttga       477

<210> SEQ ID NO 14
<211> LENGTH: 378
<212> TYPE: DNA
<213> ORGANISM: Arabidopsis thaliana
<220> FEATURE:
<223> OTHER INFORMATION: AtEC1.2a transcriptional control sequence open
      reading frame (ORF)

<400> SEQUENCE: 14
atggcttcta acacaagttt cctctttgcc accatcgcta tcctcctcgt tctcaacatc    60
tccggaagaa ctctcccgga gacggaagat tccacaaaca tagcggcaag actcaacgga   120
ggaggactaa tggagtgttg gaacgcactt tatgagctca aatcatgcac caacgaaatc   180
gttctcttct tcctcaacgg tgaaaccaaa ctcggcgtcg attgctgtca agccgtcgag   240
gtcatcacca ccgattgttg gcctgcgatg ctcacgtctc taggctttac ctctgatgaa   300
accaacgttc ttcgtggttt ctgtcaatct ccaaattccg gtggttcttc tccggcgcct   360
tcctctgtga aactttga                                                 378

<210> SEQ ID NO 15
<211> LENGTH: 378
<212> TYPE: DNA
<213> ORGANISM: Arabidopsis thaliana
<220> FEATURE:
<223> OTHER INFORMATION: AtEC1.2b transcriptional control sequence open
      reading frame (ORF)

<400> SEQUENCE: 15
atggcttcta acacaagttt cctctttgtc accgtcactc ttctcctcgt tctcaacgtc    60
tccagcagag cactcccgcc cgtggcggat tccaccaaca tagcggctag actaaccgga   120
ggaggactga tgcagtgttg ggatgcactc tacgagctga agtcatgtac taatgagatc   180
gttctcttct ttctcaacgg tgagaccaaa ctcggctacg gttgctgcaa cgccgttgat   240
gtcattacca ctgattgttg gccggcgatg cttacttctc ttggctttac actggaggaa   300
accaatgtcc tccgtggttt ctgtcaatct ccgaactccg gcggttcttc tccagctctt   360
tcccctgtca aactttga                                                 378

<210> SEQ ID NO 16
<211> LENGTH: 384
<212> TYPE: DNA
<213> ORGANISM: Arabidopsis thaliana
<220> FEATURE:
<223> OTHER INFORMATION: AtEC1.4 transcriptional control sequence open
      reading frame (ORF)

<400> SEQUENCE: 16
atggcttcga acactacttt cctcttctcc accgtcacac ttctcatcat cctcctaaac    60
accaccgtct ccggtagaga tctcccagcg gagtcatcaa ccaacatagc tgcgaggctc   120
caaagtggag gactgatgga atgctggaac gcattatacg agctgaaatc atgcaccaac   180
gagatcgttc tcttcttcct caacggtgaa acaaaacttg gtgttagttg ttgcgaatcc   240
gtagacatca tcaccaccaa ttgctggccg gcgatgctca cttctctcgg atttacgcct   300
gaggaagcta atgtccttcg tggcttttgt cagaatccaa actccggcga ctcttctccg   360
gctccgtctc ccaaaatagt ttga                                          384
```

<210> SEQ ID NO 17
<211> LENGTH: 468
<212> TYPE: DNA
<213> ORGANISM: Arabidopsis thaliana
<220> FEATURE:
<223> OTHER INFORMATION: AtEC1.5 transcriptional control sequence open
      reading frame (ORF)

<400> SEQUENCE: 17

```
atggctacta aatctacttc gaagcctctt ctgctctcat ttctaatgat gtcatatctc      60
atatcgacct ttcatgtcat cactgtcgcc gagggaagga ctctccagtt cacgaagatg     120
gctacggatc attccggcgc cggaaacttg atggactgtt ggaacgcggg gttggagctt     180
aagtcatgca ccgatgagat tgtcaagttt ttccttagtc aaaccggtac gagtgaaccg     240
ccggttaaag gtggaattga caaagattgt tgtggagcca ttgggttggt tgtgaaagat     300
tgttggtccg ttatgtttac ttctttaggg cttacgacta tggaagggaa taacttgaga     360
gagtattgtg agtttcaagc tgagaagtcg gaattatctc cttcaccggc ccgaaaact      420
ttggctttgt ctccggttga gataacgtat cccggacttg attattga                  468
```

<210> SEQ ID NO 18
<211> LENGTH: 402
<212> TYPE: DNA
<213> ORGANISM: Medicago truncatula
<220> FEATURE:
<223> OTHER INFORMATION: MtEC1.1 transcriptional control sequence open
      reading frame (ORF)

<400> SEQUENCE: 18

```
atggctttct ttttgaaact gtttattatc atatccttgt cgacaatagt tacagcaacg      60
tcattgagct caacaaaaac cctagcatca cgtttagaat tatttgatgg aagtggcccc     120
aacaacaaat gttgggagac aatgttggag cttcaacatt gtactggtga tattgttaca     180
tttttcctta atggtcagac acatcttgga tctggttgtt gtaatgctct tcttactata     240
gctcaagaat gttggggaaa tttgcttacc tcgttgggtc tcacggtaga agaagctgaa     300
attctacgtg gcttttgtgc tcgtgttgcc tctgttaaca attctctttt accatctatc     360
actgttgatg cccccttcacc tgcacctatc aacaattatt ga                       402
```

<210> SEQ ID NO 19
<211> LENGTH: 456
<212> TYPE: DNA
<213> ORGANISM: Oryza sativa
<220> FEATURE:
<223> OTHER INFORMATION: OsEC1.1 transcriptional control sequence open
      reading frame (ORF)

<400> SEQUENCE: 19

```
atggcgtgct cgggcagttt cctaccgata atgctcctgc cgctgctcct cgccggcgcc      60
gcggtggcgg gcgcgccccc gccggggctt gggctggcgc agcggctggc cgacggcgtg     120
gggcagcagc agcagcagtg ctgggaggtt ctgatggaga tcaagtcgtg cacggggagag   180
atcctcctct tcttcatcaa cggcgaggcg tacctgggcc ccggctgctg ccgcgccatc     240
cgcgtcatcg agcagagctg ctgggccacc gacgccatgc tgtccgtcat cgggttcacc     300
ccggaggagg gggacatgct caagggctac tgcgacgccg cgacgagca caagccgtcg     360
ccgcccccg cctcgccggc cgtcggctac gtcgccgtcg agagaacgc gccgtaccg       420
gccggacgga agagcctggc gctgcagcac cgttag                               456
```

```
<210> SEQ ID NO 20
<211> LENGTH: 420
<212> TYPE: DNA
<213> ORGANISM: Oryza sativa
<220> FEATURE:
<223> OTHER INFORMATION: OsEC1.2 transcriptional control sequence open
      reading frame (ORF)

<400> SEQUENCE: 20
atggcgtcct tgctgagcgt cgccgtcgtc ctcgtcgtgg tcagcgctca ggccctcgcc    60
gccgttgccg ttgccgacgc cgcgcgcgtc aacgccggcg ccgcggcctt ctcgcctgca   120
gtacccctcg gcggccggct tgacggcggc ggcggagggc tggtggagtg ctggagcgcg   180
gtggcggagc tccggtcgtg cacggacgag atcgtgctct tcttcctcaa cggcgagacg   240
acgcagctcg gcgccgggtg ctgccgcgcc gtgcgcgccg cgacgcgcga ctgctggccg   300
gccatgctcg ccgccgtcgg gttcaccgcc gaggaggccg acgtcctccg cggcctctgc   360
gacgccgagg ccgccgccgc cgccgccgac tccacgtcgc cggcgccatc ggccgcgtag   420

<210> SEQ ID NO 21
<211> LENGTH: 435
<212> TYPE: DNA
<213> ORGANISM: Oryza sativa
<220> FEATURE:
<223> OTHER INFORMATION: OsEC1.3 transcriptional control sequence open
      reading frame (ORF)

<400> SEQUENCE: 21
atggcgctcg ccgtgaagct cgccgtcctc ctactacttg ccgcggcagc agctggagga    60
agcagcacga cgaccgtgcc gccgctggag gagaggctgg gcgcggcgtt cgacgggatg   120
gcggcggcgg cggagggagg aggaggggga gggtggatga tggagtgctg gagcgcggtg   180
acgaagctgg ggtcgtgcac gaacgagatc gtgctcttct tcgtcaacgg cgagtcctac   240
ctcggcccgg actgctgcgt cgccatccgc accgtcaccc gccgctgctg gccgccatg   300 ctcgcctcca tcggcttcac cgcccaggag gccgacatcc tccgcggctt ctgcgacgcc   360
gagctcgccg ccccgccccc gccctccacc aacgcctcct ccgccgcccc cgcgccggcg   420
ccggcgtccg cttag                                                   435

<210> SEQ ID NO 22
<211> LENGTH: 716
<212> TYPE: DNA
<213> ORGANISM: Triticum aestivum
<220> FEATURE:
<223> OTHER INFORMATION: TaEC1 transcriptional control sequence cDNA
<220> FEATURE:
<221> NAME/KEY: 5'UTR
<222> LOCATION: (1)...(40)
<220> FEATURE:
<221> NAME/KEY: misc_feature
<222> LOCATION: (41)...(496)
<223> OTHER INFORMATION: TaEC1 transcriptional control sequence open
      reading frame (ORF)
<220> FEATURE:
<221> NAME/KEY: 3'UTR
<222> LOCATION: (497)...(686)
<220> FEATURE:
<221> NAME/KEY: variation
<222> LOCATION: (509)...(509)
<223> OTHER INFORMATION: n = g, a, c or t
<220> FEATURE:
<221> NAME/KEY: polyA_site
<222> LOCATION: (687)...(716)
<223> OTHER INFORMATION: poly A tail

<400> SEQUENCE: 22
```

```
gacagccagc acttgctaga gcctagaggc gatcagtacc atggcttcct ccggctcact    60
cctccccgcc ctcctcgtgc tgctcctgct cacagtcgcc gccaccgcgt cgacgactac   120 gacgacttc gtccgggcgg gcgctcctcc ggccgagctc gccgagcggc tgcagggagt    180
ggggcagcag cagtgctggg agatactgat ggacatcagg tcgtgcacgg gggagatcat   240
cctcttcttc ctcaacggcg aggcgtacct ggggcccggg tgctgccgcg ccatccgcgc   300
cgtcgagcag cactgctggg ccgcggacgc cacgctgtcc gtcatcgggt tcaccccaga   360 ggaggggac atgctcaagg gctactgcga cgccggtgac agcggcgagg ggcagcagcg   420
tggtgctttt gacggcgttg caagtgacgg cgccgtggcc gccgctgccg aaggaaggg   480 gcttggtgcc ccgtgaagct gagagtctna agtgtgtgtc cacgtccacc tgtaggttct   540
cgtgaatcct gtgatgcttc atgagttcat gtaatctttg ttgcgaagct gggaggcgag   600
ttgtgttctc tgggttttgt tcgtgtaacc cgacccgagt tggctatcgc taaccccagc   660
aaggctcgaa taatagtttc tctgccaaaa aaaaaaaaa aaaaaaaa aaaaaa        716

<210> SEQ ID NO 23
<211> LENGTH: 525
<212> TYPE: DNA
<213> ORGANISM: Hordeum vulgare
<220> FEATURE:
<223> OTHER INFORMATION: HvECA1 transcriptional control sequence open
      reading frame (ORF)

<400> SEQUENCE: 23
atggcgtctt ccggccctct ccttcccacc cttctggtgc tgctcgccgc cgccgccgca    60
accgcgtcgg cggcaggtgc gcggccggcg agtacgacga cggcgacgac gttcgtccgg   120
gccgccgacc tcgcggaccg gctggaggga cggtgtcgc agcagtgctg ggagacgctg   180
ctgcacatca gtcgtgcac gggggagatc atcctcttct tcctcaacgg cgaggcgtac   240
ctggggccgg ggtgctgccg cgccatccgc gccatcgagc agcgctgctg ggccgccgac   300
ctcatgctgt ccgtcatcgg gttcacccg gaggaggggg acatgctcaa gggctactgc   360
gacgccggcg acgacgacaa caacaacggg cctcgccata gcttcggcgg atcgtccccg   420
gccccgccgc ctcgtcgcgc tcttggcgcc gacgcgttg caaccggagc cggcaccgtg   480
gccgccgcgg cgggaaggaa agggctcggt gcgccggtag gctga              525

<210> SEQ ID NO 24
<211> LENGTH: 463
<212> TYPE: DNA
<213> ORGANISM: Arabidopsis thaliana
<220> FEATURE:
<223> OTHER INFORMATION: pAtEC1.1 transcriptional control sequence
      functionally active fragment

<400> SEQUENCE: 24
tgccttatga tttcttcggt ttcaagatga tcaaatagtt atagatttca tgctcacaca    60
tgctcattag atgtgtacat actttactta cccaaatcta ttttctcgca aagatttga   120 tggtaaagct gatttggttc tattgaacta aatcaaacga gtttcagact gagtgattct   180
aatccggccc attagcccct aaacagaccc actaattacg cagcttttaa tagagtaatt   240
acacctagtt tacccactaa accactaagc actaattatc tcacaatcta atgagcttcc   300
ctcgtaatta cttgggcttt cactctacca tttatttgta acagtcaagt ctctactgtc   360
tctatataaa ctctctaaag ttaacacaca attctcatca caaacaaatc aaccaaagca   420
acttctactc tttcttcttt cgaccttatc aatctgttga gaa                 463
```

<210> SEQ ID NO 25
<211> LENGTH: 894
<212> TYPE: DNA
<213> ORGANISM: Arabidopsis thaliana
<220> FEATURE:
<223> OTHER INFORMATION: pAtEC1.2a transcriptional control sequence
      functionally active fragment

<400> SEQUENCE: 25

```
aagcatttgc gtttggttta tcattgcgtt tatacaagga cagagatcca ctgagctgga      60
atagcttaaa accattatca gaacaaaata aaccatttt tgttaagaat cagagcatag      120
taaacaacag aaacaaccta agagaggtaa cttgtccaag aagatagcta attatatcta     180
ttttataaaa gttatcatag tttgtaagtc acaaaagatg caaataacag agaaactagg     240
agacttgaga atatacattc ttgtatattt gtattcgaga ttgtgaaaat ttgaccataa     300
gtttaaattc ttaaaaagat atatctgatc tagatgatgg ttatagactg taattttacc    360
acatgtttaa tgatggatag tgacacacat gacacatcga caacactata gcatcttatt    420
tagattacaa catgaaattt ttctgtaata catgtctttg tacataattt aaaagtaatt    480
cctaagaaat atatttatac aaggagttta aagaaaacat agcataaagt tcaatgagta    540
gtaaaaacca tatacagtat atagcataaa gttcaatgag tttattacaa aagcattggt    600
tcactttctg taacacgacg ttaaaccttc gtctccaata ggagcgctac tgattcaaca    660
tgccaatata tactaaatac gtttctacag tcaaatgctt taacgtttca tgattaagtg    720
actatttacc gtcaatcctt tcccattcct cccactaatc caacttttta attactctta    780
aatcaccact aagcttcgaa tccatccaaa accacaatat aaaaacagaa ctctcgtaac    840
tcaatcatcg caaacaaaa caaacaaaa caaaaacccc aaaagaaag aata             894
```

<210> SEQ ID NO 26
<211> LENGTH: 254
<212> TYPE: DNA
<213> ORGANISM: Arabidopsis thaliana
<220> FEATURE:
<223> OTHER INFORMATION: pAtEC1.2b transcriptional control sequence
      functionally active fragment

<400> SEQUENCE: 26

```
caagtaacca ttgactcttc gcttgtatct ttccgttaag accacctatt caatcattct      60
ctaagttaca tgatttaaga tttaagtaaa atcattaact ctctgccctc tcccacttcc     120
tccactaaaa accatcttta atcataatta aacctcaaaa atcctttcat aatcacagta     180
ttataaatag cagctcttac caaatcctct aaaccatcac acaatacaac acaaaatctt    240
caaaagaaaa caca                                                        254
```

<210> SEQ ID NO 27
<211> LENGTH: 217
<212> TYPE: DNA
<213> ORGANISM: Arabidopsis thaliana
<220> FEATURE:
<223> OTHER INFORMATION: pAtEC1.4 transcriptional control sequence
      functionally active fragment

<400> SEQUENCE: 27

```
tttcgtatgc attgtctgtt actcatcttc atcagaagcc ttaatcgcac catccaccac      60
taatcattta ctttcactta tccctcccca ctaataaacc ttttaattac tctttaatat    120
ccactaacac aacaaatcct tccacaaaca cactataaat accaaaccat cacaagctag    180
tctaatcaca ctaaaattcc aaacaaaaac cacacca                              217
```

<210> SEQ ID NO 28
<211> LENGTH: 251
<212> TYPE: DNA
<213> ORGANISM: Arabidopsis thaliana
<220> FEATURE:
<223> OTHER INFORMATION: pAtEC1.5 transcriptional control sequence
      functionally active fragment

<400> SEQUENCE: 28
gggtttccat aaagcccaat ttagttggcc caatagcttg caaaactggg cgtaacggat     60
aatttaataa agacacggta aatgcttaga tagaggatta gagggtaatt aaattaacca    120
cgatcactgt gataattact acaacattaa acgacaaaaa aacttttcgt ctccctcata    180
atcttctact atatattcgt cacatcacac tcataatctc ttacaaaaaa tccataacac    240
aaaaagaagc a                                                        251

<210> SEQ ID NO 29
<211> LENGTH: 1000
<212> TYPE: DNA
<213> ORGANISM: Medicago truncatula
<220> FEATURE:
<223> OTHER INFORMATION: pMtEC1.1 transcriptional control sequence
      functionally active fragment

<400> SEQUENCE: 29
atcctcaaca tttctatcgc aaatagctac gagtttctat cttccatcac cgccgcatct     60
tcgccgccgc gatgcctcta tgtaactcac aaagcgtctt catcggtgtc gccgttgagc    120
aacactattt tccttcagca tcaacttcct ctttgcgacg gtggccggag caaaggcctt    180
gacggaggag tagacatctt gcgactcttg ttcggaggta agtgtgacgg cggggtgctt    240
atgggtttgt gatgtgtgag ggaggaagct tatggtggtg gacgattgtt ctctctctct    300
ctctctcgct atgttacagg cttttttatt ttattttaaa aacagatgtg ccacgtggca    360
cgttctgatt gactatgtca catgacatag cccgccttaa tgtcacggaa gtggaatccc    420
tcatatatca ccaaataagt ctccaattat gtgtaacaaa atggcagcaa tcgattcacc    480
ctttgaagtc aatattagcc gttatatttg taacaacaac aactcaattt gtaagtgaac    540 gttttttaatt agcaattaaa gattccatct gcataacgta catatacata cacaatatga    600
gatcatatat acaatcaaat attcaagtgt cattttattt tataaataaa ttaaaaaaaa    660
aacaagtttc attgcaataa aaatactaat aatccagctt cacactctct tatttaattt    720
aattttccac cagggtccct ttcagctcct gactttcaca gttacacttt tatatatcac    780
tcttaattta tttctttaat tccttaactg aaaaataacc gttggaaact ctatagacga    840
tagtcataca aattgggtat agtaaaagct ttatagaacc taatggccaa acatatgcta    900
tataaattat catcacccgt tcctcatttt tcatcacatc aaataatctc tatccctcac    960
tcaaagtatc attcccatta tcactaaata atctccagcc                        1000

<210> SEQ ID NO 30
<211> LENGTH: 700
<212> TYPE: DNA
<213> ORGANISM: Oryza sativa
<220> FEATURE:
<223> OTHER INFORMATION: pOsEC1.1 transcriptional control sequence
      functionally active fragment

<400> SEQUENCE: 30
atgctctgtt cctttttcaag gaatggaatg atggatgaat gttcacgttc ttgagttcct     60

```
aaatggtact aattttgcaa aaactttcta tatgtgtttt ttgttaagaa tgttgtttta    120
aacccatctt ttcactttat aatatttaat taaatcgttc gtaccctcga atagttattg    180
caaattatac ttaactattc agtcattcag cacaaaagaa cagggccatg aaattgtaat    240
actagtacat ttctgttctt ttcttttctt tttgaggttg tctgaaacac ctgtatctta    300
aactatcgca gactagccaa tgagtcgtac tcacctgaaa ctgaaaccaa gtgattaacc    360
aagctggttc gacagtaatt ccatccataa tgcagctccg gagcccttca tatcctgcat    420
gttactcaaa caacatcccc acctcctcat ttcctctccc ctattgcatt gcataattgc    480
agaagattaa gccgctaatg cataattaca cattatttgt gtccactaat tttccctttc    540
ccacacgcta cgaaactcaa aagccggcct cctcgcctcc ttccctgaac gttactaatc    600
gcgtcatgta taaatacaga gcttgcccac gcaccggcac attgcatcgc actacgcaca    660
tctacacgat acccaagcag caaagctaga aagaaaaacc                         700
```

<210> SEQ ID NO 31
<211> LENGTH: 450
<212> TYPE: DNA
<213> ORGANISM: Oryza sativa
<220> FEATURE:
<223> OTHER INFORMATION: pOsEC1.2 transcriptional control sequence
      functionally active fragment

<400> SEQUENCE: 31

```
tcgagttacc tgactcctga ctgctgcaat tgcatatttg tcagtatcct gaaccatttg     60
ataagcaatc gatcatacat gcatgattca ttcttgtatg tgaatctaaa tttatagatg    120
catcataagt gttgccgtta ctcttttgca atgtgctaat actaattgaa gcgcactaat    180
caataattaa ctcataactc gttgaagttc cactactagt accagtacca ggagcatgtg    240
atctgctcat cttaattaac gatccgttaa tctaatccct ttgcctccac cgttctgcat    300
gcgcgccgtc agctaatgat tcgattaatt acgtcccccg cgagcttacg ttaccactaa    360
gtacgtactt aacatattat cctatataag tgtgagcaat tagcaggagt taatcgtgtc    420
cacttaacat acatcgcaca gcattcagca                                     450
```

<210> SEQ ID NO 32
<211> LENGTH: 1095
<212> TYPE: DNA
<213> ORGANISM: Oryza sativa
<220> FEATURE:
<223> OTHER INFORMATION: pOsEC1.3 transcriptional control sequence
      functionally active fragment

<400> SEQUENCE: 32

```
aagcttccaa atggacaaca tgcaacaata caaactacat acatgagtgt tgagaccatc     60
ccctggagaa aggataaatc aaacaatcca gatataacta gatgtgtacc ccgcgcgttg    120
ctgcggaaga attatgtaat aatatagtag atatgagttc taaaattttc ttcaaacca    180 actatatgat ttcttttcat gtgtttatat attttttacc tttattaatt atccaaatgt    240
cataaataat tggggttgtat ggtgtatctt ttggtggaaa gagatgcaat ttacacttttt    300 gatgaatcat ccaaagtctt aaaagaattg agttgatgtg gcttcacgac agaagagaga    360
attagcatta actacacgta gtggggatga acttgataga tatatataga tataggattt    420
gttttcgttt gccataatat gaagagaaaa taatactatt tgtttattaa gcctgtaaga    480
aactctgtaa tatagtaatt ttgtgcggta aggatatatt atcagtcgct gcagaaacgc    540
tatagggcag catttttgctg ggtaaatagg attgaagcaa aataggtgag gaagccaaac    600
```

```
tgattacttt gcaatagttt gaagcaaaat accaaaaatt ttattttttgc cattgacaca    660 ctaggtgagc aattttgtta ccacgtccat gtgctgattt aaagtttttt ttttaaaaaa    720
gaaacttatt ttttttcttt gccacaatat aaagctaaaa tatttgtcat taactgatcc    780
tgttgcaaac aatgaattt acccccaccat agctaaatta actcatgatt aataaataag    840
cctgtaagtt acagaactga agaaactctg taataataat aattgatcac taagaatatg    900
atcagtcgcc gccattgatc actaagctag tgcagtgtaa tggcaatgga cgccactacc    960
atcaacaatg gcagcgatcc catccccttc cccttcctcg cgccctatat aaccacagct    1020
cgccggcgat cgatcactgc accatcagct cccacaaacc cagctaacca agtttaattg    1080
ccaccaagct cacca                                                    1095

<210> SEQ ID NO 33
<211> LENGTH: 8
<212> TYPE: DNA
<213> ORGANISM: Artificial Sequence
<220> FEATURE:
<223> OTHER INFORMATION: synthetic EC1 promoter nucleotide sequence
      motif #1

<400> SEQUENCE: 33 ccactaat                                                            8

<210> SEQ ID NO 34
<211> LENGTH: 21
<212> TYPE: DNA
<213> ORGANISM: Artificial Sequence
<220> FEATURE:
<223> OTHER INFORMATION: synthetic wheat GAPDH intron-spanning PCR
      primer TaGAP1

<400> SEQUENCE: 34
agggtggtgc caagaaggtc a                                             21

<210> SEQ ID NO 35
<211> LENGTH: 20
<212> TYPE: DNA
<213> ORGANISM: Artificial Sequence
<220> FEATURE:
<223> OTHER INFORMATION: synthetic wheat GAPDH intron-spanning PCR
      primer TaGAP2

<400> SEQUENCE: 35
tatccccact cgttgtcgta                                               20

<210> SEQ ID NO 36
<211> LENGTH: 21
<212> TYPE: DNA
<213> ORGANISM: Artificial Sequence
<220> FEATURE:
<223> OTHER INFORMATION: synthetic PCR primer TaEC1fw2

<400> SEQUENCE: 36
ccgagcggct gcagggagtg g                                             21

<210> SEQ ID NO 37
<211> LENGTH: 22
<212> TYPE: DNA
<213> ORGANISM: Artificial Sequence
<220> FEATURE:
<223> OTHER INFORMATION: synthetic PCR primer TaEC1rev2

<400> SEQUENCE: 37
gcgtcggagt agcccttgag ca                                            22
```

<210> SEQ ID NO 38
<211> LENGTH: 26
<212> TYPE: DNA
<213> ORGANISM: Artificial Sequence
<220> FEATURE:
<223> OTHER INFORMATION: synthetic Arabidopsis actin (At2g37620)
      intron-spanning PCR primer Act3fw

<400> SEQUENCE: 38
gatttggcat cacactttct acaatg                                          26

<210> SEQ ID NO 39
<211> LENGTH: 21
<212> TYPE: DNA
<213> ORGANISM: Artificial Sequence
<220> FEATURE:
<223> OTHER INFORMATION: synthetic Arabidopsis actin (At2g37620)
      intron-spanning PCR primer Act3rev

<400> SEQUENCE: 39
gttccaccac tgagcacaat g                                               21

<210> SEQ ID NO 40
<211> LENGTH: 21
<212> TYPE: DNA
<213> ORGANISM: Artificial Sequence
<220> FEATURE:
<223> OTHER INFORMATION: synthetic AtEC1.1 gene specific PCR
      amplification primer AtEC1.1fw

<400> SEQUENCE: 40
acagtgacag ctcgccctct c                                               21

<210> SEQ ID NO 41
<211> LENGTH: 24
<212> TYPE: DNA
<213> ORGANISM: Artificial Sequence
<220> FEATURE:
<223> OTHER INFORMATION: synthetic AtEC1.1 gene specific PCR
      amplification primer AtEC1.1rev

<400> SEQUENCE: 41
agtcattgcc atcatagtaa cctt                                            24

<210> SEQ ID NO 42
<211> LENGTH: 21
<212> TYPE: DNA
<213> ORGANISM: Artificial Sequence
<220> FEATURE:
<223> OTHER INFORMATION: synthetic AtEC1.2a/b gene specific PCR
      amplification primer AtEC1.2a/bfw

<400> SEQUENCE: 42
agtttcctct ttgccaccat c                                               21

<210> SEQ ID NO 43
<211> LENGTH: 21
<212> TYPE: DNA
<213> ORGANISM: Artificial Sequence
<220> FEATURE:
<223> OTHER INFORMATION: synthetic AtEC1.2a/b gene specific PCR
      amplification primer AtEC1.2a/brev

<400> SEQUENCE: 43
caccgttgag gaagaagaga a                                               21

<210> SEQ ID NO 44
<211> LENGTH: 24
<212> TYPE: DNA
<213> ORGANISM: Artificial Sequence
<220> FEATURE:
<223> OTHER INFORMATION: synthetic AtEC1.4 gene specific PCR
      amplification primer AtEC1.4fw

<400> SEQUENCE: 44
ccagcggagt catcaaccaa cata                                          24

<210> SEQ ID NO 45
<211> LENGTH: 22
<212> TYPE: DNA
<213> ORGANISM: Artificial Sequence
<220> FEATURE:
<223> OTHER INFORMATION: synthetic AtEC1.4 gene specific PCR
      amplification primer AtEC1.4rev

<400> SEQUENCE: 45
ggagacggag ccggagaaga gt                                            22

<210> SEQ ID NO 46
<211> LENGTH: 21
<212> TYPE: DNA
<213> ORGANISM: Artificial Sequence
<220> FEATURE:
<223> OTHER INFORMATION: synthetic AtEC1.5 gene specific PCR
      amplification primer AtEC1.5fw

<400> SEQUENCE: 46
gcgccggaaa cttgatggac t                                             21

<210> SEQ ID NO 47
<211> LENGTH: 21
<212> TYPE: DNA
<213> ORGANISM: Artificial Sequence
<220> FEATURE:
<223> OTHER INFORMATION: synthetic AtEC1.5 gene specific PCR
      amplification primer AtEC1.5rev

<400> SEQUENCE: 47
ggcgccggtg aaggagataa t                                             21

<210> SEQ ID NO 48
<211> LENGTH: 23
<212> TYPE: DNA
<213> ORGANISM: Artificial Sequence
<220> FEATURE:
<223> OTHER INFORMATION: synthetic AtEC1.1 genomic DNA PCR amplification
      promoter primer pAtEC1.1

<400> SEQUENCE: 48
tgccttatga tttcttcggt ttc                                           23

<210> SEQ ID NO 49
<211> LENGTH: 28
<212> TYPE: DNA
<213> ORGANISM: Artificial Sequence
<220> FEATURE:
<223> OTHER INFORMATION: synthetic AtEC1.1 genomic DNA PCR
      amplification gene specific primer AtEC1.1rev1

<400> SEQUENCE: 49
tcagagtcat tgccatcaca gtaacctt                                      28

<210> SEQ ID NO 50
<211> LENGTH: 22

```
<212> TYPE: DNA
<213> ORGANISM: Artificial Sequence
<220> FEATURE:
<223> OTHER INFORMATION: synthetic AtEC1.2a genomic DNA PCR
      amplification promoter primer pAtEC1.2a

<400> SEQUENCE: 50
aagcatttgc gtttggttta tc                                            22

<210> SEQ ID NO 51
<211> LENGTH: 20
<212> TYPE: DNA
<213> ORGANISM: Artificial Sequence
<220> FEATURE:
<223> OTHER INFORMATION: synthetic AtEC1.2a genomic DNA PCR
      amplification terminator primer tAtEC1.2a

<400> SEQUENCE: 51
aatgcggttt tagtcacacg                                               20

<210> SEQ ID NO 52
<211> LENGTH: 22
<212> TYPE: DNA
<213> ORGANISM: Artificial Sequence
<220> FEATURE:
<223> OTHER INFORMATION: synthetic PCR amplification gene specific
      primer AtEC1.1-PstI

<400> SEQUENCE: 52
ccatttctct gcagattgat aa                                            22

<210> SEQ ID NO 53
<211> LENGTH: 22
<212> TYPE: DNA
<213> ORGANISM: Artificial Sequence
<220> FEATURE:
<223> OTHER INFORMATION: synthetic PCR amplification gene specific
      primer AtEC1.2a-BglII

<400> SEQUENCE: 53
ccatagatct ttcttttggg gg                                            22

<210> SEQ ID NO 54
<211> LENGTH: 20
<212> TYPE: DNA
<213> ORGANISM: Artificial Sequence
<220> FEATURE:
<223> OTHER INFORMATION: synthetic colony PCR gene specific primer GUS
      start rev

<400> SEQUENCE: 54
atccagactg aatgcccaca                                               20

<210> SEQ ID NO 55
<211> LENGTH: 20
<212> TYPE: DNA
<213> ORGANISM: Artificial Sequence
<220> FEATURE:
<223> OTHER INFORMATION: synthetic genomic DNA AtEC1.1 promoter and open
      reading frame amplification primer E1F

<400> SEQUENCE: 55
gccttatgat ttcttcggtt                                               20

<210> SEQ ID NO 56
<211> LENGTH: 20
<212> TYPE: DNA
<213> ORGANISM: Artificial Sequence
```

```
<220> FEATURE:
<223> OTHER INFORMATION: synthetic genomic DNA AtEC1.1 promoter and open
      reading frame amplification primer E1R

<400> SEQUENCE: 56
gcaggagtgt aaagatgaat                                                    20

<210> SEQ ID NO 57
<211> LENGTH: 27
<212> TYPE: DNA
<213> ORGANISM: Artificial Sequence
<220> FEATURE:
<223> OTHER INFORMATION: synthetic genomic DNA AtEC1.1 promoter and open
      reading frame second amplification modified primer EC1-PF2

<400> SEQUENCE: 57
ccccgaattc cttatgattt cttcggt                                            27

<210> SEQ ID NO 58
<211> LENGTH: 24
<212> TYPE: DNA
<213> ORGANISM: Artificial Sequence
<220> FEATURE:
<223> OTHER INFORMATION: synthetic genomic DNA AtEC1.1 promoter and open
      reading frame second amplification modified primer EC1-R

<400> SEQUENCE: 58
ctcggatccg ggttagaagg agaa                                               24

<210> SEQ ID NO 59
<211> LENGTH: 18
<212> TYPE: DNA
<213> ORGANISM: Artificial Sequence
<220> FEATURE:
<223> OTHER INFORMATION: synthetic sequencing primer GFP-seq for
      C-terminal fusion of EGFP and AtEC1.1 cloned fragment

<400> SEQUENCE: 59
ccagttccac caggattg                                                      18

<210> SEQ ID NO 60
<211> LENGTH: 17
<212> TYPE: DNA
<213> ORGANISM: Artificial Sequence
<220> FEATURE:
<223> OTHER INFORMATION: synthetic sequencing primer LH1 for C-terminal
      fusion of EGFP and AtEC1.1 cloned fragment

<400> SEQUENCE: 60
cccaagatct ggccctt                                                       17

<210> SEQ ID NO 61
<211> LENGTH: 21
<212> TYPE: DNA
<213> ORGANISM: Artificial Sequence
<220> FEATURE:
<223> OTHER INFORMATION: synthetic T-DNA PCR primer GUS3

<400> SEQUENCE: 61
gcgtggtgat gtggagtatt g                                                  21

<210> SEQ ID NO 62
<211> LENGTH: 21
<212> TYPE: DNA
<213> ORGANISM: Artificial Sequence
<220> FEATURE:
<223> OTHER INFORMATION: synthetic T-DNA PCR primer GUS4
```

-continued

```
<400> SEQUENCE: 62
tcaccgaagt tcatgccagt c                                              21

<210> SEQ ID NO 63
<211> LENGTH: 20
<212> TYPE: DNA
<213> ORGANISM: Artificial Sequence
<220> FEATURE:
<223> OTHER INFORMATION: synthetic T-DNA PCR primer bar-fw

<400> SEQUENCE: 63
ccgtaccgag ccgcaggaac                                                20

<210> SEQ ID NO 64
<211> LENGTH: 23
<212> TYPE: DNA
<213> ORGANISM: Artificial Sequence
<220> FEATURE:
<223> OTHER INFORMATION: synthetic T-DNA PCR primer bar-rev

<400> SEQUENCE: 64
cagatctcgg tgacgggcag gac                                            23

<210> SEQ ID NO 65
<211> LENGTH: 20
<212> TYPE: DNA
<213> ORGANISM: Artificial Sequence
<220> FEATURE:
<223> OTHER INFORMATION: synthetic genomic DNA AtEC1.1 open reading
      frame and 3'-UTR PCR amplification primer 1-1fwXbaI

<400> SEQUENCE: 65
atctgtctag aaatggcttc                                                20

<210> SEQ ID NO 66
<211> LENGTH: 23
<212> TYPE: DNA
<213> ORGANISM: Artificial Sequence
<220> FEATURE:
<223> OTHER INFORMATION: synthetic genomic DNA AtEC1.1 open reading
      frame and 3'-UTR PCR amplification primer 1-1revXbaI

<400> SEQUENCE: 66
tttattctag aaagtaataa cag                                            23

<210> SEQ ID NO 67
<211> LENGTH: 24
<212> TYPE: DNA
<213> ORGANISM: Artificial Sequence
<220> FEATURE:
<223> OTHER INFORMATION: synthetic genomic DNA AtEC1.2a open reading
      frame and 3'-UTR PCR amplification primer At2a-BglIIfw

<400> SEQUENCE: 67
aaagaaagat ctatggcttc taac                                           24

<210> SEQ ID NO 68
<211> LENGTH: 24
<212> TYPE: DNA
<213> ORGANISM: Artificial Sequence
<220> FEATURE:
<223> OTHER INFORMATION: synthetic genomic DNA AtEC1.2a open reading
      frame and 3'-UTR PCR amplification primer At2a-Salrev

<400> SEQUENCE: 68
tcattagtcg actttgcata catc                                           24
```

```
<210> SEQ ID NO 69
<211> LENGTH: 8
<212> TYPE: DNA
<213> ORGANISM: Artificial Sequence
<220> FEATURE:
<223> OTHER INFORMATION: synthetic EC1 promoter nucleotide sequence
      motif #2

<400> SEQUENCE: 69 ktaattam                                                                   8

<210> SEQ ID NO 70
<211> LENGTH: 17
<212> TYPE: PRT
<213> ORGANISM: Artificial Sequence
<220> FEATURE:
<223> OTHER INFORMATION: portion of EC1 transcriptional control sequence
      polypeptide consensus sequence
<221> NAME/KEY: VARIANT
<222> LOCATION: (1)...(1)
<223> OTHER INFORMATION: Xaa = Leu or Ile
<221> NAME/KEY: VARIANT
<222> LOCATION: (2)...(7)
<223> OTHER INFORMATION: Xaa = any amino acid
<221> NAME/KEY: VARIANT
<222> LOCATION: (8)...(8)
<223> OTHER INFORMATION: Xaa = Ala or Ser
<221> NAME/KEY: VARIANT
<222> LOCATION: (9)...(9)
<223> OTHER INFORMATION: Xaa = Ile, Leu of Val
<221> NAME/KEY: VARIANT
<222> LOCATION: (10)...(15)
<223> OTHER INFORMATION: Xaa = any amino acid

<400> SEQUENCE: 70

Xaa Xaa Xaa Xaa Cys Cys Xaa Xaa Xaa Xaa Xaa Xaa Xaa Xaa Xaa Cys
 1               5                  10                  15

Trp

<210> SEQ ID NO 71
<211> LENGTH: 15
<212> TYPE: PRT
<213> ORGANISM: Artificial Sequence
<220> FEATURE:
<223> OTHER INFORMATION: portion of EC1 transcriptional control sequence
      polypeptide consensus sequence
<221> NAME/KEY: VARIANT
<222> LOCATION: (1)...(1)
<223> OTHER INFORMATION: Xaa = Ile, Leu or Val
<221> NAME/KEY: VARIANT
<222> LOCATION: (3)...(3)
<223> OTHER INFORMATION: Xaa = Phe or Leu
<221> NAME/KEY: VARIANT
<222> LOCATION: (5)...(14)
<223> OTHER INFORMATION: Xaa = any amino acid

<400> SEQUENCE: 71

Xaa Gly Xaa Thr Xaa Xaa Glu Xaa Xaa Xaa Leu Xaa Xaa Xaa Cys
 1               5                  10                  15

<210> SEQ ID NO 72
<211> LENGTH: 23
<212> TYPE: DNA
<213> ORGANISM: Artificial Sequence
<220> FEATURE:
<223> OTHER INFORMATION: synthetic Oligo(dT)-23

<400> SEQUENCE: 72
tttttttttt tttttttttt ttt                                                 23
```

```
<210> SEQ ID NO 73
<211> LENGTH: 20
<212> TYPE: DNA
<213> ORGANISM: Artificial Sequence
<220> FEATURE:
<223> OTHER INFORMATION: synthetic Oligo(dT)-20

<400> SEQUENCE: 73
tttttttttt tttttttttt                                              20

<210> SEQ ID NO 74
<211> LENGTH: 456
<212> TYPE: DNA
<213> ORGANISM: Triticum aestivum
<220> FEATURE:
<223> OTHER INFORMATION: TaEC1 transcriptional control sequence open
      reading frame (ORF)

<400> SEQUENCE: 74
atggcttcct ccggctcact cctccccgcc ctcctcgtgc tgctcctgct cacagtcgcc      60
gccaccgcgt cgacgactac gacgaccttc gtccgggcgg gcgctcctcc ggccgagctc     120
gccgagcggc tgcagggagt ggggcagcag cagtgctggg agatactgat ggacatcagg     180
tcgtgcacgg gggagatcat cctcttcttc ctcaacggcg aggcgtacct ggggcccggg     240
tgctgccgcg ccatccgcgc cgtcgagcag cactgctggg ccgcggacgc cacgctgtcc     300
gtcatcgggt tcaccccaga ggagggggac atgctcaagg gctactgcga cgccggtgac     360
agcggcgagg ggcagcagcg tggtgctttt gacggcgttg caagtgacgg cgccgtggcc     420
gccgctgccg gaaggaaggg gcttggtgcc ccgtga                              456
```